(12) United States Patent
Ethelfeld

(10) Patent No.: US 8,029,469 B2
(45) Date of Patent: Oct. 4, 2011

(54) EXTERNAL INSERTER FOR TRANSCUTANEOUS DEVICE

(75) Inventor: Erik Winkel Ethelfeld, Copenhagen (DK)

(73) Assignee: Novo Nordisk A/S, Bagsvaerd (SK)

( * ) Notice: Subject to any disclaimer, the term of this patent is extended or adjusted under 35 U.S.C. 154(b) by 1121 days.

(21) Appl. No.: 11/250,233

(22) Filed: Oct. 14, 2005

(65) Prior Publication Data

US 2006/0095014 A1    May 4, 2006

Related U.S. Application Data

(63) Continuation of application No. PCT/DK2004/000335, filed on May 10, 2004.

(30) Foreign Application Priority Data

May 8, 2003 (EP) .................................. 03388034

(51) Int. Cl.
*A61M 31/00* (2006.01)

(52) U.S. Cl. .................... 604/136; 604/506; 604/93.01; 604/180

(58) Field of Classification Search ............. 604/288.03, 604/506, 136, 180, 93.01, 131, 134
See application file for complete search history.

(56) References Cited

U.S. PATENT DOCUMENTS

| 55,711 | A | 6/1866 | Regester |
| 69,546 | A | 10/1867 | DeFrost |
| 123,740 | A | 2/1872 | Stevens |
| 858,001 | A | 6/1907 | Howe |
| 2,605,765 | A | 8/1952 | Kollsman |
| 2,960,097 | A | 11/1960 | Scheffler |
| 2,980,032 | A | 4/1961 | Schneider |
| 3,705,601 | A | 12/1972 | Arisland |
| 4,016,879 | A | 4/1977 | Mellor |

(Continued)

FOREIGN PATENT DOCUMENTS

CA        2239457        12/1999

(Continued)

OTHER PUBLICATIONS

Non-Final Rejection Mailed on Jan. 5, 2007 in U.S. Appl. No. 11/266,904, filed Nov. 4, 2005 by Ethelfeld et al.

(Continued)

*Primary Examiner* — Theodore J Stigell
*Assistant Examiner* — Michael J Anderson
(74) *Attorney, Agent, or Firm* — Wesley A. Nicolas; Marc A. Began

(57) ABSTRACT

A medical device is provided, comprising a first unit and a releasably attachable second unit. The first unit comprises a mounting surface adapted for application to the skin of a subject, and a transcutaneous device comprising a distal pointed end adapted to penetrate the skin of the subject, wherein the transcutaneous device has a first position in which the distal end is retracted relative to the mounting surface, and a second position in which the distal end projects relative to the mounting surface. The second unit comprises actuatable driving means adapted to move the transcutaneous device from the first position to the second position when the driving means is actuated with the second unit attached to the first unit. By this arrangement the first unit can be applied to the skin of the subject using the second unit as a gripping and handling means, whereafter the driving means can be actuated for insertion of the transcutaneous device.

19 Claims, 14 Drawing Sheets

U.S. PATENT DOCUMENTS

| | | |
|---|---|---|
| 4,077,405 A | 3/1978 | Haerten et al. |
| 4,137,020 A | 1/1979 | Ito et al. |
| 4,245,634 A | 1/1981 | Albisser et al. |
| 4,262,824 A | 4/1981 | Hrynewycz |
| 4,340,048 A | 7/1982 | Eckenhoff |
| 4,370,305 A | 1/1983 | Affonso |
| 4,378,015 A * | 3/1983 | Wardlaw ............... 604/137 |
| 4,399,824 A | 8/1983 | Davidson |
| 4,402,407 A | 9/1983 | Maly |
| 4,519,792 A | 5/1985 | Dawe |
| 4,529,401 A | 7/1985 | Leslie et al. |
| 4,544,369 A | 10/1985 | Skakoon et al. |
| 4,552,561 A | 11/1985 | Eckenhoff et al. |
| 4,645,491 A | 2/1987 | Evans |
| 4,657,490 A | 4/1987 | Abbott |
| 4,710,170 A | 12/1987 | Haber |
| 4,734,092 A | 3/1988 | Millerd |
| 4,753,651 A | 6/1988 | Eckenhoff |
| 4,755,173 A | 7/1988 | Konopka et al. |
| 4,788,556 A | 11/1988 | Hoisington et al. |
| 4,871,351 A | 10/1989 | Feingold |
| 4,877,034 A | 10/1989 | Atkins et al. |
| 4,886,499 A | 12/1989 | Cirelli et al. |
| 4,894,054 A | 1/1990 | Miskinyar |
| 4,928,528 A | 5/1990 | Marques |
| 4,994,078 A | 2/1991 | Jarvik |
| 5,008,110 A | 4/1991 | Benecke et al. |
| 5,049,146 A | 9/1991 | Bringham et al. |
| 5,076,890 A | 12/1991 | Balembois |
| 5,122,116 A | 6/1992 | Kriesel et al. |
| 5,122,201 A | 6/1992 | Frazier et al. |
| 5,149,340 A | 9/1992 | Waycuilis |
| 5,169,390 A | 12/1992 | Athayde et al. |
| 5,211,201 A | 5/1993 | Kamen et al. |
| 5,224,843 A | 7/1993 | van Lintel |
| 5,256,157 A | 10/1993 | Samiotes et al. |
| 5,336,052 A | 8/1994 | Zöllner et al. |
| 5,390,671 A | 2/1995 | Lord et al. |
| 5,391,950 A | 2/1995 | Krawczak |
| 5,482,473 A | 1/1996 | Lord et al. |
| 5,485,917 A | 1/1996 | Early |
| 5,494,415 A | 2/1996 | Morita |
| 5,514,095 A | 5/1996 | Brightbill et al. |
| 5,527,287 A | 6/1996 | Miskinyar |
| 5,527,288 A | 6/1996 | Gross et al. |
| 5,568,806 A | 10/1996 | Cheney, II et al. |
| 5,584,808 A | 12/1996 | Healy |
| 5,584,813 A | 12/1996 | Livingston et al. |
| 5,586,085 A | 12/1996 | Lichte |
| 5,609,572 A | 3/1997 | Lang |
| 5,647,853 A | 7/1997 | Feldmann et al. |
| 5,720,391 A | 2/1998 | Dohm et al. |
| 5,776,109 A | 7/1998 | Urrutia |
| 5,814,020 A | 9/1998 | Gross |
| 5,851,197 A | 12/1998 | Marano et al. |
| 5,858,001 A | 1/1999 | Tsals et al. |
| 5,860,952 A | 1/1999 | Quinn |
| 5,913,856 A | 6/1999 | Chia et al. |
| 5,925,017 A | 7/1999 | Kriesel et al. |
| 5,928,194 A | 7/1999 | Maget |
| 5,931,814 A | 8/1999 | Alex et al. |
| 5,941,611 A | 8/1999 | Trzmiel et al. |
| 5,954,643 A | 9/1999 | Van Antwerp et al. |
| 5,957,895 A | 9/1999 | Sage et al. |
| 5,968,011 A | 10/1999 | Larsen et al. |
| 5,997,501 A | 12/1999 | Gross et al. |
| 6,045,534 A | 4/2000 | Jacobsen et al. |
| 6,060,319 A | 5/2000 | Deetz et al. |
| 6,074,369 A | 6/2000 | Sage et al. |
| 6,083,196 A | 7/2000 | Trautman et al. |
| 6,088,619 A | 7/2000 | Hein et al. |
| 6,099,512 A | 8/2000 | Urrutia |
| 6,120,492 A | 9/2000 | Finch et al. |
| 6,123,519 A | 9/2000 | Kato et al. |
| 6,126,637 A | 10/2000 | Kriesel et al. |
| 6,132,755 A | 10/2000 | Eicher et al. |
| 6,165,155 A | 12/2000 | Jacobsen et al. |
| 6,241,704 B1 | 6/2001 | Peterson et al. |
| 6,270,478 B1 | 8/2001 | Mernøe |
| 6,280,148 B1 | 8/2001 | Zengerle et al. |
| 6,293,925 B1 | 9/2001 | Safabash et al. |
| 6,302,866 B1 | 10/2001 | Marggi |
| 6,302,869 B1 | 10/2001 | Klitgaard |
| 6,358,731 B1 | 3/2002 | Hsu |
| 6,364,865 B1 | 4/2002 | Lavi et al. |
| 6,485,461 B1 | 11/2002 | Mason et al. |
| 6,500,150 B1 | 12/2002 | Gross et al. |
| 6,551,276 B1 | 4/2003 | Mann et al. |
| 6,554,791 B1 | 4/2003 | Cartledge et al. |
| 6,555,986 B2 | 4/2003 | Moberg |
| 6,558,351 B1 | 5/2003 | Steil et al. |
| 6,589,229 B1 | 7/2003 | Connelly et al. |
| 6,613,015 B2 | 9/2003 | Sandstrom et al. |
| 6,622,037 B2 | 9/2003 | Kasano |
| 6,656,159 B2 | 12/2003 | Flaherty |
| 6,716,192 B1 | 4/2004 | Orosz |
| 6,740,059 B2 | 5/2004 | Flaherty |
| 6,749,587 B2 | 6/2004 | Flaherty |
| 6,808,691 B1 | 10/2004 | Herve et al. |
| 6,818,178 B2 | 11/2004 | Kohl et al. |
| 6,878,136 B2 | 4/2005 | Fleury et al. |
| 6,949,084 B2 | 9/2005 | Marggi et al. |
| 6,960,192 B1 | 11/2005 | Flaherty et al. |
| 7,052,483 B2 | 5/2006 | Wojcik |
| 7,070,580 B2 | 7/2006 | Nielsen |
| 7,097,631 B2 * | 8/2006 | Trautman et al. ............... 604/46 |
| 7,097,690 B2 | 8/2006 | Usher et al. |
| 7,141,023 B2 | 11/2006 | Diermann et al. |
| 7,144,384 B2 | 12/2006 | Gorman et al. |
| 7,303,073 B2 | 12/2007 | Raynal-Olive et al. |
| 7,744,570 B2 | 6/2010 | Fangrow |
| 2001/0025168 A1 | 9/2001 | Gross et al. |
| 2002/0040083 A1 | 4/2002 | Kuwaki et al. |
| 2002/0040208 A1 | 4/2002 | Flaherty et al. |
| 2002/0055711 A1 | 5/2002 | Lavi et al. |
| 2002/0064468 A1 | 5/2002 | Wade |
| 2002/0123740 A1 | 9/2002 | Flaherty et al. |
| 2002/0161332 A1 | 10/2002 | Ramey |
| 2002/0169416 A1 | 11/2002 | Gonnelli et al. |
| 2003/0009131 A1 | 1/2003 | Van Antwerp et al. |
| 2003/0009133 A1 | 1/2003 | Ramey |
| 2003/0029501 A1 | 2/2003 | Williamson et al. |
| 2003/0060781 A1 | 3/2003 | Mogensen et al. |
| 2003/0065308 A1 | 4/2003 | Lebel et al. |
| 2003/0069546 A1 | 4/2003 | Sandstrom et al. |
| 2003/0073952 A1 | 4/2003 | Flaherty et al. |
| 2003/0088238 A1 | 5/2003 | Poulsen et al. |
| 2003/0114797 A1 | 6/2003 | Vaillancourt et al. |
| 2003/0135159 A1 | 7/2003 | Daily et al. |
| 2003/0167035 A1 | 9/2003 | Flaherty et al. |
| 2003/0187395 A1 | 10/2003 | Gabel et al. |
| 2003/0194328 A1 | 10/2003 | Bryant et al. |
| 2003/0199823 A1 | 10/2003 | Bobroff et al. |
| 2003/0216686 A1 | 11/2003 | Lynch et al. |
| 2003/0236498 A1 | 12/2003 | Gross et al. |
| 2004/0051674 A1 | 3/2004 | Mahringer |
| 2004/0087240 A1 | 5/2004 | Chen et al. |
| 2004/0098068 A1 | 5/2004 | Carbunaru et al. |
| 2004/0115068 A1 | 6/2004 | Hansen et al. |
| 2004/0116905 A1 | 6/2004 | Pedersen et al. |
| 2004/0127844 A1 | 7/2004 | Flaherty |
| 2004/0158207 A1 | 8/2004 | Hunn et al. |
| 2004/0162521 A1 | 8/2004 | Bengtsson |
| 2004/0171403 A1 | 9/2004 | Mikkola |
| 2004/0199123 A1 | 10/2004 | Nielsen |
| 2004/0204673 A1 | 10/2004 | Flaherty |
| 2004/0220497 A1 | 11/2004 | Findlay et al. |
| 2004/0220536 A1 | 11/2004 | VanTassel et al. |
| 2004/0260233 A1 | 12/2004 | Garibotto et al. |
| 2005/0006309 A1 | 1/2005 | Effenhauser et al. |
| 2005/0022274 A1 | 1/2005 | Campbell et al. |
| 2005/0077225 A1 | 4/2005 | Usher et al. |
| 2005/0101933 A1 | 5/2005 | Marrs et al. |
| 2005/0171513 A1 | 8/2005 | Mann et al. |
| 2005/0203461 A1 | 9/2005 | Flaherty et al. |
| 2005/0240154 A1 | 10/2005 | Mogensen et al. |
| 2006/0015063 A1 | 1/2006 | Butikofer et al. |

| | | | |
|---|---|---|---|
| 2006/0017576 A1 | 1/2006 | Gordon et al. | |
| 2006/0020300 A1 | 1/2006 | Nghiem et al. | |
| 2006/0142698 A1 | 6/2006 | Ethelfeld | |
| 2006/0200073 A1 | 9/2006 | Radmer et al. | |
| 2006/0264835 A1 | 11/2006 | Nielsen et al. | |
| 2007/0021733 A1 | 1/2007 | Hansen et al. | |
| 2007/0073228 A1 | 3/2007 | Mernoe et al. | |
| 2007/0104596 A1 | 5/2007 | Preuthun et al. | |
| 2007/0112301 A1 | 5/2007 | Preuthun et al. | |
| 2008/0009805 A1 | 1/2008 | Ethelfeld | |
| 2009/0163874 A1 | 6/2009 | Krag et al. | |

FOREIGN PATENT DOCUMENTS

| | | |
|---|---|---|
| CN | 1612758 | 5/2005 |
| DE | 2552446 | 5/1977 |
| DE | 10255817 | 6/2004 |
| DK | PA 2003 00696 | 5/2003 |
| DK | PA 2003 00697 | 5/2003 |
| EP | 20060277 | 3/1986 |
| EP | 398583 | 11/1990 |
| EP | 568176 | 11/1993 |
| EP | 937475 | 8/1999 |
| EP | 1177802 | 7/2000 |
| EP | 1177802 | 2/2002 |
| EP | 1256356 | 11/2002 |
| EP | 1329233 | 7/2003 |
| EP | 1475113 | 11/2004 |
| EP | 1527792 | 5/2005 |
| GB | 2020735 | 11/1979 |
| GB | 2212387 | 7/1989 |
| JP | 2000-104659 | 4/2000 |
| JP | 2000-513259 | 10/2000 |
| JP | 2000-515394 | 11/2000 |
| JP | 2002-505601 | 2/2002 |
| WO | WO 90/07942 | 7/1990 |
| WO | WO 96/07397 | 3/1996 |
| WO | WO 96/30679 | 10/1996 |
| WO | WO 97/21457 | 12/1996 |
| WO | WO 98/57683 | 12/1998 |
| WO | WO 99/62576 | 12/1999 |
| WO | 02/015965 | 8/2000 |
| WO | 02/055132 | 10/2000 |
| WO | 02/045574 | 12/2000 |
| WO | 02/10457 | 4/2001 |
| WO | 02/81012 | 4/2001 |
| WO | WO02/005889 | 7/2001 |
| WO | WO 02/02165 | 1/2002 |
| WO | WO 02/04048 | 1/2002 |
| WO | WO 02/15889 | 2/2002 |
| WO | WO 02/40083 | 5/2002 |
| WO | WO02/47746 | 6/2002 |
| WO | WO 02/070024 | 9/2002 |
| WO | WO03000696 | 1/2003 |
| WO | WO03000697 | 1/2003 |
| WO | WO03/026726 | 4/2003 |
| WO | WO03/026728 | 4/2003 |
| WO | WO 03/080169 | 10/2003 |
| WO | WO03/089028 | 10/2003 |
| WO | WO 03/090509 | 11/2003 |
| WO | WO 03/099358 | 12/2003 |
| WO | WO 2004/009160 | 1/2004 |
| WO | WO2004/029457 | 4/2004 |
| WO | WO2004/030728 | 4/2004 |
| WO | WO2004/098682 | 11/2004 |
| WO | WO 2004/098683 | 11/2004 |
| WO | WO2004/098684 | 11/2004 |
| WO | WO 2004/101071 | 11/2004 |
| WO | WO2005/002649 | 1/2005 |
| WO | WO 2005/011779 | 2/2005 |
| WO | WO 2005/025652 | 3/2005 |
| WO | WO2005/037185 | 4/2005 |
| WO | WO2005/037350 | 4/2005 |
| WO | WO2005/039673 | 5/2005 |
| WO | WO2005/094919 | 10/2005 |
| WO | WO 2005/123186 | 12/2005 |
| WO | WO 2005/123189 | 12/2005 |
| WO | WO2006/060277 | 6/2006 |
| WO | WO 2006/067217 | 6/2006 |
| WO | WO 2006/077263 | 7/2006 |
| WO | WO2006/089958 | 8/2006 |
| WO | WO 2006/120253 | 11/2006 |
| WO | WO 2006/123329 | 11/2006 |
| WO | WO2007/122207 | 11/2007 |
| WO | WO 2009/021950 | 2/2009 |

OTHER PUBLICATIONS

Final Rejection Mailed on Sep. 11, 2007 in U.S. Appl. No. 11/266,904, filed Nov. 4, 2005 by Ethelfeld et al.
Final Rejection Mailed on Oct. 30, 2009 in U.S. Appl. No. 11/266,905, filed Nov. 4, 2005 by Ethelfeld et al.
Non-Final Rejection Mailed on Mar. 18, 2009 in U.S. Appl. No. 11/266,905, filed Nov. 4, 2005 by Ethelfeld et al.
Non-Final Rejection Mailed on Aug. 25, 2008 in U.S. Appl. No. 11/266,905, filed Nov. 4, 2005 by Ethelfeld et al.
Final Rejection Mailed on Oct. 5, 2007 in U.S. Appl. No. 11/266,905, filed Nov. 4, 2005 by Ethelfeld et al.
Non-Final Rejection Mailed on Mar. 27, 2007 in U.S. Appl. No. 11/266,905, filed Nov. 4, 2005 by Ethelfeld et al.
Non-Final Rejection Mailed on Mar. 28, 2008 in U.S. Appl. No. 11/266,821, filed Nov. 4, 2005 by Erik Winkel Ethelfeld.
Final Rejection Mailed on Jul. 18, 2008 in U.S. Appl. No. 11/266,821, filed Nov. 4, 2005 by Erik Winkel Ethelfeld.
Non-Final Rejection Mailed on Jan. 29, 2009 in U.S. Appl. No. 11/266,821, filed Nov. 4, 2005 by Erik Winkel Ethelfeld.
International Search Report mailed Jul. 5, 2007 in international application No. PCT/EP2007/053923.
International Preliminary Examination Report issued in connection with counterpart PCT Application No. PCT/EP2006/062301, mailed Nov. 22, 2007.
International Search Report and Written Opinion issued in connection with counterpart international application No. PCT/EP2006/062301, mailed Nov. 2, 2006.
International Search Report mailed May 24, 2006 in international application No. PCT/EP2006/050410.
Office Action Issued in Connection With Counterpart Danish Application No. PA 2005 00703, Mailed Mar. 3, 2006.
CN 1612758 English Abstract, published Feb. 6, 2008.
DE 10255817 English Abstract, published Jun. 17, 2004.
JP 2000-104659 Machine Translation, published Apr. 11, 2000.
Final Office Action mailed Apr. 16, 2010 in U.S. Appl. No. 12/303,307, filed Feb. 20, 2009 by Krag.
Non-Final Office Action mailed Nov. 27, 2009 in U.S. Appl. No. 12/303,307, filed Feb. 20, 2009 by Krag.
Non-Final Office Action mailed Apr. 6, 2010 in U.S. Appl. No. 12/298,253, filed Dec. 8, 2008 by Krag et al.
Final Office Action mailed Apr. 28, 2010 in U.S. Appl. No. 12/066,712, filed Mar. 13, 2008 by Hansen et al.
Non-Final Office Action mailed Oct. 27, 2009 in U.S. Appl. No. 12/066,712, filed Mar. 13, 2008 by Hansen et al.
Non-Final Office Action mailed Apr. 10, 2009 in U.S. Appl. No. 12/066,712, filed Mar. 13, 2008 by Hansen et al.
Final Office Action mailed Jul. 16, 2010 in U.S. Appl. No. 11/913,689, filed Dec. 12, 2007 by Hansen et al.
Non-Final Office Action mailed Mar. 15, 2010 in U.S. Appl. No. 11/913,689, filed Dec. 12, 2007 by Hansen et al.
Final Office Action mailed Nov. 25, 2009 in U.S. Appl. No. 11/913,689, filed Dec. 12, 2007 by Hansen et al.
Non-Final Office Action mailed May 8, 2009 in U.S. Appl. No. 11/913,689, filed Dec. 12, 2007 by Hansen et al.
Non-Final Office Action mailed Apr. 30, 2010 in U.S. Appl. No. 11/911,213, filed Oct. 11, 2007 by Nielsen et al.
Non-Final Office Action mailed Jul. 24, 2009 in U.S. Appl. No. 11/911,213, filed Oct. 11, 2007 by Nielsen et al.
Final Office Action mailed Nov. 17, 2009 in U.S. Appl. No. 11/816,729, filed Nov. 15, 2007 by Larsen et al.
Non-Final Office Action mailed Apr. 17, 2009 in U.S. Appl. No. 11/816,729, filed Nov. 15, 2007 by Larsen et al.
Non-Final Office Action mailed Jul. 23, 2010 in U.S. Appl. No. 11/813,433, filed Apr. 30, 2008 by Teisen-Simony et al.
Non-Final Office Action mailed Apr. 28, 2010 in U.S. Appl. No. 11/813,381, filed Apr. 11, 2008 by Teisen-Simony et al.

Final Office Action mailed Nov. 3, 2009 in U.S. Appl. No. 11/792,355, filed Apr. 23, 2008 by Ethelfeld et al.
Non-Final Office Action mailed Feb. 17, 2009 in U.S. Appl. No. 11/792,355, filed Apr. 23, 2008 by Ethelfeld et al.
Final Office Action mailed Dec. 29, 2009 in U.S. Appl. No. 11/663,048, filed Nov. 15, 2007 by Thorkild et al.
Non-Final Office Action mailed Apr. 17, 2009 in U.S. Appl. No. 11/663,048, filed Nov. 15, 2007 by Thorkild et al.
Notice of Abandonment mailed Oct. 23, 2007 in U.S. Appl. No. 11/662,905, filed Sep. 22, 2005 by Ahm et al.
Non-Final Office Action mailed May 19, 2010 in U.S. Appl. No. 11/541,348, filed Sep. 29, 2006 by Preuthun et al.
Final Office Action mailed Jan. 8, 2010 in U.S. Appl. No. 11/541,348, filed Sep. 29, 2006 by Preuthun et al.
Non-Final Office Action mailed May 22, 2009 in U.S. Appl. No. 11/541,348, filed Sep. 29, 2006 by Preuthun et al.
Response and Amendment filed Jan. 29, 2009 in U.S. Appl. No. 11/541,348, filed Sep. 29, 2006 by Preuthun et al.
Final Office Action mailed Oct. 29, 2008 in U.S. Appl. No. 11/541,348, filed Sep. 29, 2006 by Preuthun et al.
Response and Amendment filed Jul. 16, 2008 in U.S. Appl. No. 11/541,348, filed Sep. 29, 2006 by Preuthun et al.
Non-Final Office Action mailed Apr. 18, 2008 in U.S. Appl. No. 11/541,348, filed Sep. 29, 2006 by Preuthun et al.
Final Office Action mailed May 5, 2010 in U.S. Appl. No. 11/540,842, filed Sep. 29, 2006 by Preuthun et al.
Non-Final Office Action mailed Sep. 28, 2009 in U.S. Appl. No. 11/540,842, filed Sep. 29, 2006 by Preuthun et al.
Response and Amendment filed Aug. 7, 2009 in U.S. Appl. No. 11/540,842, filed Sep. 29, 2006 by Preuthun et al.
Final Office Action mailed May 13, 2009 in U.S. Appl. No. 11/540,842, filed Sep. 29, 2006 by Preuthun et al.
Response and Amendment filed Mar. 11, 2009 in U.S. Appl. No. 11/540,842, filed Sep. 29, 2006 by Preuthun et al.
Non-Final Office Action mailed Dec. 12, 2008 in U.S. Appl. No. 11/540,842, filed Sep. 29, 2006 by Preuthun et al.
Response and Amendment filed Oct. 10, 2008 in U.S. Appl. No. 11/540,842, filed Sep. 29, 2006 by Preuthun et al.
Final Office Action mailed Jul. 11, 2008 in U.S. Appl. No. 11/540,842, filed Sep. 29, 2006 by Preuthun et al.
Response and Amendment filed May 20, 2008 in U.S. Appl. No. 11/540,842, filed Sep. 29, 2006 by Preuthun et al.
Non-Final Office Action mailed Feb. 25, 2008 in U.S. Appl. No. 11/540,842, filed Sep. 29, 2006 by Preuthun et al.
Final Office Action mailed Aug. 5, 2009 in U.S. Appl. No. 11/407,647 filed Apr. 20, 2006 by Hansen et al.
Non-Final Office Action mailed Feb. 6, 2009 in U.S. Appl. No. 11/407,647, filed Apr. 20, 2006 by Hansen et al.
Final Office Action mailed Sep. 29, 2008 in U.S. Appl. No. 11/407,647, filed Apr. 20, 2006 by Hansen et al.
Non-Final Office Action mailed Feb. 28, 2008 in U.S. Appl. No. 11/407,647, filed Apr. 20, 2006 by Hansen et al.
Non-Final Office Action mailed Aug. 19, 2010 in U.S. Appl. No. 11/266,905, filed Nov. 4, 2005 by Ethelfeld et al.
Notice of Abandonment mailed Oct. 12, 2010 in U.S. Appl. No. 11/266,904, filed Nov. 14, 2005 by Ethelfeld et al.
Second Advisory Action mailed Aug. 13, 2008 in U.S. Appl. No. 11/266,904, filed Nov. 4, 2005 by Ethelfeld et al.
First Advisory Action mailed Dec. 28, 2007 in U.S. Appl. No. 11/266,904, filed Nov. 4, 2005 by Ethelfeld et al.
Requirement for Restriction mailed May 22, 2006 in U.S. Appl. No. 11/266,904, filed Nov. 4, 2005 by Ethelfeld et al.
Notice of Allowance mailed Jul. 15, 2009 in U.S. Appl. No. 11/266,821, filed Nov. 4, 2005 by Ethelfeld et al.
Notice of Abandonment mailed Aug. 31, 2010 in U.S. Appl. No. 10/566,795, filed Aug. 30, 2006 by Radmer et al.
Final Office Action mailed May 4, 2009 in U.S. Appl. No. 10/566,795, filed Aug. 30, 2006 by Radmer et al.
Non-Final Office Action mailed Oct. 17, 2008 in U.S. Appl. No. 10/566,795, filed Aug. 30, 2006 by Radmer et al.
US 6,197,009, 03/2001, Steg (withdrawn)

* cited by examiner

Fig. 3A
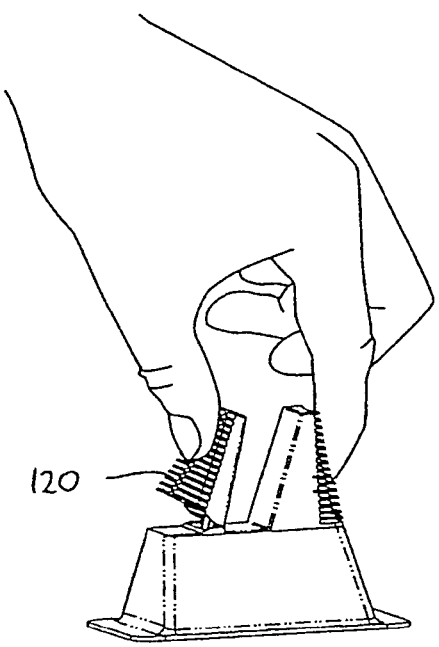
Fig. 3B
Fig. 3C
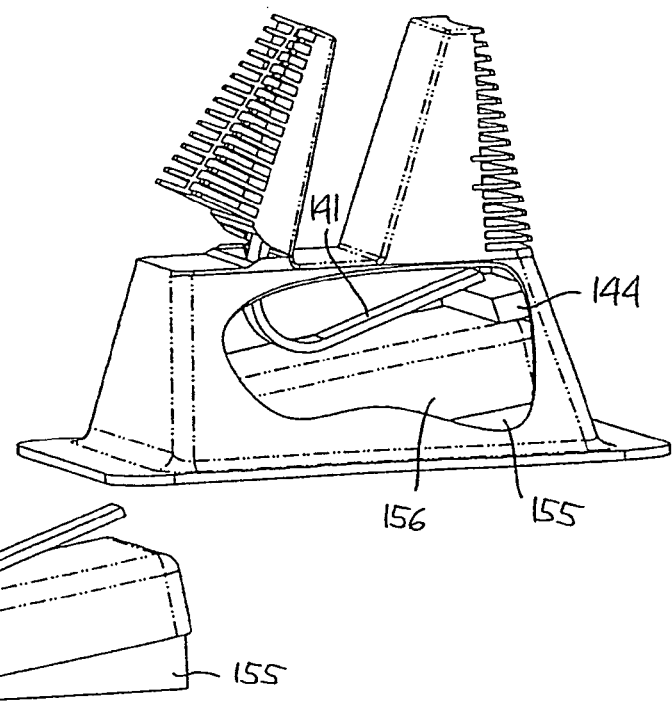

120

150

144
145
156

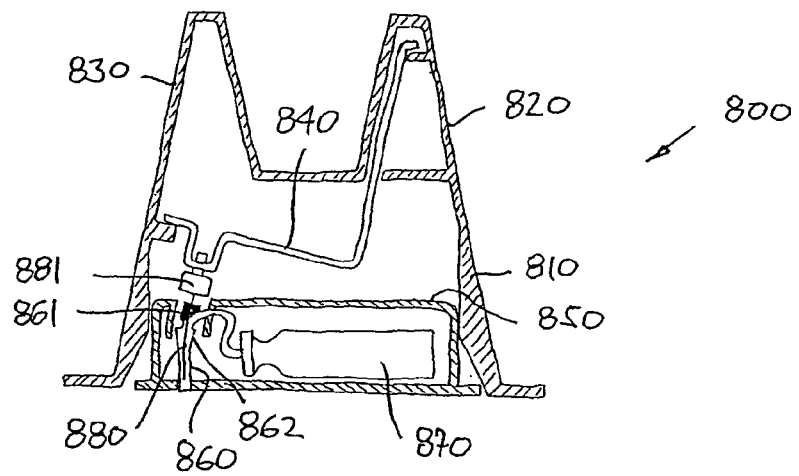
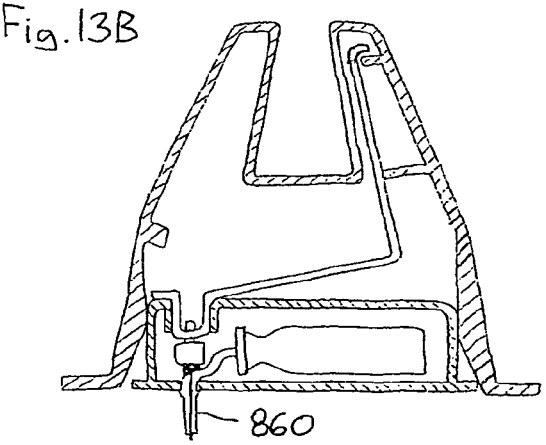
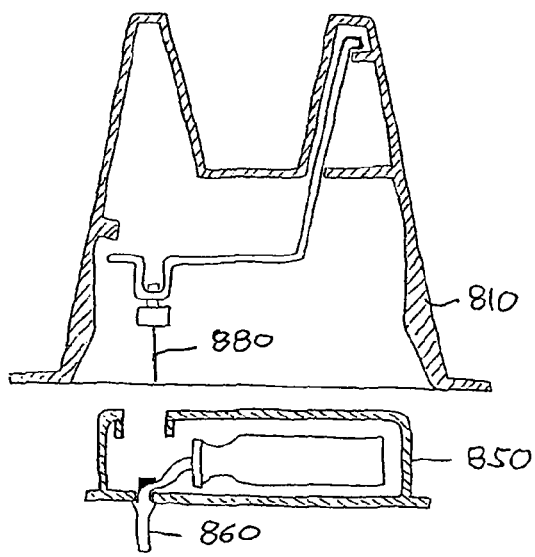

EXTERNAL INSERTER FOR TRANSCUTANEOUS DEVICE

CROSS REFERENCE TO RELATED APPLICATIONS

This application is a continuation of International Application no. PCT/DK2004/000335 filed May 10, 2004 and claims priority of European application no. 03388034.5 filed May 8, 2005.

The present invention generally relates to the insertion of transcutaneous access devices such as needles, needle-like members and cannulas. More specifically, the invention relates to insertion of a transcutaneous access device at a selected site within the body of a subject for subcutaneous, intravenous, intramuscular or intradermal delivery of a drug to the subject, the transcutaneous device being carried by a device comprising a mounting surface adapted for application to the skin of the subject. Especially, the invention relates to insertion of an infusion needle or cannula for the infusion of a drug, to insertion of a needle-formed sensor, as well as to insertion of insertion needles for easy placement of a device such as a sensor through the skin of a subject.

BACKGROUND OF THE INVENTION

In the disclosure of the present invention reference is mostly made to the treatment of diabetes by injection or infusion of insulin, however, this is only an exemplary use of the present invention.

Portable drug delivery devices for delivering a drug to a patient are well known and generally comprise a reservoir adapted to contain a liquid drug and having an outlet in fluid communication with a hollow infusion needle, as well as expelling means for expelling a drug out of the reservoir and through the skin of the subject via the hollow needle. Such devices are often termed infusion pumps.

Basically, infusion pumps can be divided into two classes. The first class comprises durable infusion pumps which are relatively expensive pumps intended for 3-4 years use, for which reason the initial cost for such a pump often is a barrier to this type of therapy. Although more complex than traditional syringes and pens, the pump offer the advantages of continuous infusion of insulin, precision in dosing and optionally programmable delivery profiles and user actuated bolus infusions in connections with meals.

Addressing the above problem, several attempts have been made to provide a second class of drug infusion devices that are low in cost and convenient to use. Some of these devices are intended to be partially or entirely disposable and may provide many of the advantages associated with an infusion pump without the attendant cost and inconveniencies, e.g. the pump may be prefilled thus avoiding the need for filling or refilling a drug reservoir. Examples of this type of infusion devices are known from U.S. Pat. Nos. 4,340,048 and 4,552,561 (based on osmotic pumps), U.S. Pat. No. 5,858,001 (based on a piston pump), U.S. Pat. No. 6,280,148 (based on a membrane pump), U.S. Pat. No. 5,957,895 (based on a flow restrictor pump (also know as a bleeding hole pump)), U.S. Pat. No. 5,527,288 (based on a gas generating pump), or U.S. Pat. No. 5,814,020 (based on a swellable gel) which all in the last decades have been proposed for use in inexpensive, primarily disposable drug infusion devices, the cited documents being incorporated by reference.

The disposable pumps generally comprise a skin-contacting mounting surface adapted for application to the skin of a subject by adhesive means, and with the infusion needle arranged such that in a situation of use it projects from the mounting surface to thereby penetrate the skin of the subject, whereby the place where the needle penetrates the skin is covered while the appliance is in use.

The infusion needle may be arranged to permanently project from the mounting surface such that the needle is inserted simultaneously with the application of the infusion pump. Examples of this configuration can be found in U.S. Pat. Nos. 2,605,765, 4,340,048 and in EP 1 177 802. Although this configuration provides a simple and cost-effective solution, the actual user-performed piercing of the tissue with the needle is often problematic as people who are not experts in medicine are usually insufficiently practised to place such a needle correctly and they often suffer from a fear of the likely pain. Although not relating specifically to infusion pumps, U.S. Pat. No. 5,851,197 discloses an injector in which an infusion set comprising a skin-mountable surface with a protruding needle can be inserted, the injector upon actuation driving the entire infusion set into contact with a skin portion whereby the needle is inserted.

Addressing the above problem, infusion pump devices have been proposed in which the pump device is supplied to the user with the needle in a retracted state, i.e. with the distal pointed end of the needle "hidden" inside the pump device, this allowing the user to place the pump device on the skin without the possibility of observing the needle. When first the needle is hidden, at least some of the fear is overcome making the introduction of the needle in a second step less problematic. U.S. Pat. Nos. 5,858,001 and 5,814,020 disclose infusion devices of this type in which an infusion needle is arranged in an upper housing portion pivotably arranged relative to a base plate portion. In this way the user can introduce the needle by pressing the upper portion into engagement with the base plate portion.

To further reduce the fear and pain associated with the introduction of the needle, many recent pump devices have been provided with actuatable needle insertion means, which just has to be released by the user after which e.g. spring means quickly will advance the needle through the skin.

For example, U.S. Pat. No. 5,957,895 discloses a liquid drug delivery device comprising a bent injection needle which is adapted to project through a needle aperture in the bottom surface of the housing in a situation of use. A movable needle carrier is disposed in the housing for carrying the injection needle and for causing the injection end of the needle to project through the needle aperture upon movement of the needle carrier.

U.S. Pat. No. 5,931,814 discloses an infusion device having a housing with a drug reservoir, an infusion needle (or cannula) communicating with the reservoir, means for inserting the needle, and pump means for discharging the reservoir contents through the needle. The needle is fixed relative to the housing and projects beyond the lower skin-contacting surface of the housing to the depth required for injection. The needle is surrounded by a protective element which is moved by spring means from a first end position in which the protective device projects beyond the lower surface of the housing and beyond the needle to a second end position in which the protective device does not project beyond the underside of the casing. An advantage of this design is that the needle is arranged in a fixed position relative to the reservoir. WO 02/15965 discloses a similar infusion device in which a base plate member acts as a protecting element until an upper part of the device, to which the needle is fixed, is moved down into engagement with the base plate member.

In the devices disclosed in U.S. Pat. Nos. 5,957,895 and 5,931,814 the needle is automatically inserted by the release of pre-tensioned spring means arranged within the devices, whereas in the device known from WO 02/15965 the needle is inserted by the user actively moving the hidden needle. Although the automatic needle insertion means adds convenience for the user and may serve to overcome needle fear, such means also adds to the complexity and bulkiness of the device, the first issue adding to the cost of the device, the latter issue making the device less attractive and convenient to wear.

Before turning to the disclosure of the present invention, a different type of device relying on the insertion of a needle or needle-like structure will be described.

Although drug infusion pumps, either disposable or durable, may provide convenience of use and improved treatment control, it has long been an object to provide a drug infusion system for the treatment of e.g. diabetes which would rely on closed loop control, i.e. being more or less fully automatic, such a system being based on the measurement of a value indicative of the condition treated, e.g. the blood glucose level in case of insulin treatment of diabetes.

A given monitor system for measuring the concentration of a given substance may be based on invasive or non-invasive measuring principles. An example of the latter would be a non-invasive glucose monitor arranged on the skin surface of a patient and using near-IR spectroscopy, however, the present invention is concerned with the introduction of a transcutaneous device such as a needle-formed sensor element.

The sensor may be placed subcutaneously being connected to external equipment by wiring or the substance (fluid) to be analysed may be transported to an external sensor element, both arrangements requiring the placement of a subcutaneous component, the present invention addressing both arrangements. However, for simplicity the term "sensor" is used in the following for both types of sensor elements.

Turning to the sensor elements per se, relatively small and flexible electrochemical sensors have been developed for subcutaneous placement of sensor electrodes in direct contact with patient blood or other extra-cellular fluid (see for example U.S. Pat. No. 5,482,473), wherein such sensors can be used to obtain periodic or continuous readings over a period of time. Insertion devices for this type of sensors are described in, among others, U.S. Pat. Nos. 5,390,671, 5,391, 950, 5,568,806 and 5,954,643 which hereby are incorporated by reference.

More specifically, U.S. Pat. No. 5,954,643 discloses an insertion set comprising a mounting base supporting a proximal end of a flexible thin film sensor, the sensor including a distal segment with sensor electrodes thereon which protrudes from the mounting base for transcutaneous placement, wherein the sensor distal segment is slidably carried by a slotted insertion needle fitted through the assembled base. Placement of the insertion set against the patient's skin causes the insertion needle to pierce the skin to carry the sensor electrodes to the desired subcutaneous site, after which the insertion needle can be slidably withdrawn from the insertion set. A similar arrangement is known from U.S. Pat. No. 5,568, 806.

DISCLOSURE OF THE INVENTION

Having regard to the above-identified problems, it is an object of the present invention to provide an insertion means for a transcutaneous access device (in the following also termed a transcutaneous device) which would allow for easy and swift, automatic insertion of the transcutaneous device, yet providing a compact transcutaneous device-carrying device which can be manufactured cost effectively.

Correspondingly, a medical device is provided, comprising a first unit and a releasably attachable or attached second unit. The first unit comprises a mounting surface adapted for application to the skin of a subject, and a transcutaneous device comprising a distal pointed end adapted to penetrate the skin of the subject, wherein the transcutaneous device has a first position in which the distal end is retracted relative to the mounting surface, and a second position in which the distal end projects relative to the mounting surface. The second unit comprises actuatable driving means adapted to move the transcutaneous device from the first position to the second position when the driving means is actuated with the second unit attached to the first unit. By this arrangement the first unit can be applied to the skin of the subject where after the driving means can be actuated for insertion of the transcutaneous device.

Thus, a medical device is provided allowing for easy handling as a user can use the second unit to grip and handle the combined device during operation thereof, just as the second unit can be optimized for inserting the transcutaneous device with a speed and force which minimizes user discomfort as well as for ease of use during activation of the driving means as the drive means is no longer a part of the device which is carried by the patient and for which a compact design is of great importance. Correspondingly, as the first unit does not comprise any transcutaneous device drive means, the size can be further reduced and the design can be optimized for cost effective manufacture.

The transcutaneous device may be in the form of a pointed hollow infusion needle, a micro needle array, a pointed needle sensor, or a combination of a relatively flexible per se blunt cannula or sensor device with a pointed insertion needle may provide a pointed transcutaneous device, the insertion needle being retractable after insertion of the blunt portion of the transcutaneous device. The cannula is advantageously soft and flexible relative to the insertion needle which typically is a solid steel needle. In the disclosure of the present invention as well as in the description of the exemplary embodiments, reference will mostly be made to a transcutaneous device in the form of an infusion needle.

The first and second units may be releasably attached to each other by any suitable means allowing the combined device initially to be handled and applied against the skin as a unitary device, yet allowing the units to be separated by the user, e.g. by a frictional fit, releasable gripping means with or without locking means, or by breakable attachment means such as adhesives or welding. The mounting surface may be held in contact with the skin surface by use of additional means (e.g. adhesive bandages), however, preferably the mounting surface comprises adhesive means for attaching the first unit directly to the skin of the subject.

The driving means may in the form of spring means which is arranged in an activated state when supplied to the user or can be arranged in an activated state by the user, the second unit comprising trigger means for releasably retaining the spring means in the actuated state (e.g. compressed or bend), wherein the trigger means is operable to release the spring means for moving the needle from the first position to the second position. It should be emphasized that the activated state not necessarily is a stable state in which the spring means can be left, but a state which may require that an actuation input (e.g. a force applied by the user) is upheld, i.e. the spring means may resume an initial state if the actuation input is removed. The spring means may be any elastically compressible or deformable driving means, e.g. metal or polymer member, elastomeric foam or gas.

When the driving means comprises spring means, the second unit may comprise actuation means actuatable from a first condition through an intermediate condition to a second condition, whereby actuation of the actuation means from the first to the intermediate condition causes activation of the driving means, and actuation of the actuation means from the intermediate to the second condition causes release of the activated spring means thereby moving the needle from the first position to the second position. By this arrangement the actuation means may serve as a user interface such that the user will not have to directly engage the spring means just as the user input may be transformed, e.g. from one type of movement to another.

Advantageously the actuation means comprises an actuating element (e.g. an element which can be gripped or actuated by the user) which is moved from a first position through an intermediate position to a second position, preferably corresponding to a substantially non-composite movement (e.g. a unidirectional linear or rotational movement and which may be with or without an intermediate lockable state). In an alternative arrangement actuation of the actuation means from the first through the intermediate to the second condition is accomplished by moving two actuation elements against each.

The second unit may be provided with an interior space for at least partially accommodating the first unit and an opening through which the first member can be moved when detached from the second unit, the mounting surface facing away from the interior space. By the term partially is defined that a portion of the first unit may project from the opening of the cavity. In this way the second unit may serve in partial as a container for the first unit. In order to fully provide a container for the first unit, the second unit comprises a circumferential portion surrounding the opening, and to which portion a seal member is releasably attached, thereby providing a closed space for the first unit. In exemplary embodiments when it is desirable to sterilize the entire first unit, the seal member may be penetratable for sterilizing gases (e.g. ethylene oxide or dry steam), yet being non-penetratable for germs. By this arrangement the first unit can serve as a packaging for the second unit, this further reducing costs as well as overall size. Advantageously, the circumferential portion defines a general plane, this allowing e.g. foil-, film- or paper-like materials to be used as sealing members.

Advantageously, the second unit comprises a housing defining the interior space, this allowing the driving means to be arranged between an upper portion of the first unit (i.e. opposite the mounting surface) and a portion of the housing. In this configuration the housing may serve as the user interface providing the above-discussed actuation means for the driving means.

The mounting surface is advantageously generally planar and arranged substantially corresponding to the general plane. When such a mounting surface comprises adhesive means for attaching the first unit to the skin of the subject, the seal member may advantageously be releasably attached to the adhesive means, this arrangement avoiding the use of a separate releasable liner on the adhesive. In case a separate liner is provided, the liner and the seal member may be arranged such that pealing off the seal member automatically result in the liner being peeled of, this irrespective of the position of the mounting surface. The term "generally planar" is meant to include embodiments in which the mounting surface is somewhat concave or convex.

The needle may be introduced through or into the skin at any desired angel relative to the mounting surface (and thus the skin surface), e.g. generally perpendicular to the mounting surface.

As indicated above, the present invention may be utilized in combination with a number of different types of devices.

For example, for a medical device as described above the needle may be in the form of a hollow infusion needle, the first unit further comprising a reservoir adapted to contain a liquid drug and comprising in a situation of use an outlet in fluid communication with the infusion needle, as well as expelling means for expelling a drug out of the reservoir and through the skin of the subject via the hollow needle. The reservoir and the expelling means may be of any suitable type, e.g. of any of the types described in the above-referred documents.

The transcutaneous device may also be in the form of a needle sensor comprising sensor means capable of being influenced by a body substance and producing a signal corresponding thereto. The sensor means may be of any suitable type, e.g. of any of the types described in the above-referred documents.

In a further embodiment the first unit comprises a transcutaneous device comprising a transcutaneous member (e.g. a soft cannula or a sensor) in combination with a co-axially or co-linearly arranged pointed insertion needle, the insertion needle and the transcutaneous member being arranged to be simultaneously moved by the driving means from their respective first position to their respective second position when the driving means is actuated, wherein the insertion needle is arranged to be moveable away from the distal end of the transcutaneous member when the cannula and the insertion needle have been moved to their second position. Advantageously the insertion needle is attached to or gripped by the driving means, this allowing the insertion needle to be removed from the first unit together with the second unit.

In a further aspect of the invention, a method of applying a medical device to a skin surface of a subject is provided, the method comprising the steps of: (a) providing a medical device having a first unit and a releasably attached second unit, wherein the first unit comprises a generally planar mounting surface comprising adhesive means for adhering the first unit to the skin of the subject, a transcutaneous device comprising a distal pointed end adapted to penetrate the skin of the subject, wherein the transcutaneous device has a first retracted position relative to the second unit, and a second position in which the distal end projects relative to the second unit. The second unit comprises an interior space accommodating the first unit and having an opening through which the first unit can be moved when detached from the second unit, the second unit having a circumferential portion defining a general plane and surrounding the opening, the mounting surface being arranged interiorly in respect of the general plane or substantially corresponding to the general plane, a seal member releasably attached to the circumferential portion, thereby providing a closed space for the first unit, and actuatable driving means adapted to move the transcutaneous device from the first position to the second position when the driving means is actuated with the second unit attached to the first unit. The method comprises the further steps of (b) removing the seal member, (c) arranging the medical device in contact with the skin of the subject, (d) actuating the driving means thereby moving the transcutaneous device into the skin of the subject, and (e) removing the second unit from the first unit.

Depending on whether the mounting surface initially is positioned interiorly in respect of the general plane or substantially corresponding to the general plane, the adhesive surface will be placed in contact with the skin surface either when the device is actuated (thereby moving the first unit towards the skin) or when the device is initially placed on the skin surface.

As used herein, the term "drug" is meant to encompass any drug-containing flowable medicine capable of being passed through a delivery means such as a hollow needle in a controlled manner, such as a liquid, solution, gel or fine suspension. Representative drugs include pharmaceuticals such as peptides, proteins (e.g. insulin, insulin analogues, C-peptide), and hormones, biologically derived or active agents, hormonal and gene based agents, nutritional formulas and other substances in both solid (dispensed) or liquid form. In the description of the exemplary embodiments reference will be made to the use of insulin. Correspondingly, the term "subcutaneous" infusion is meant to encompass any method of transcutaneous delivery to a subject. Further, the term needle (when not otherwise specified) defines a piercing member (including an array of micro needles) adapted to penetrate the skin of a subject.

BRIEF DESCRIPTION OF THE DRAWINGS

In the following the invention will be further described with references to the drawings, wherein FIGS. 3A-3C shows a third state of use corresponding to FIGS. 2A-2C, FIGS. 13A-13C show in cross-sections a further embodiment of a medical device.

In the figures like structures are identified by like reference numerals.

DESCRIPTION OF EXEMPLARY EMBODIMENTS

When in the following terms as "upper" and "lower", "right" and "left", "horizontal" and "vertical" or similar relative expressions are used, these only refer to the appended figures and not to an actual situation of use.

FIGS. 1-4 show in schematic representations perspective views of different states of use of a medical device in accordance with the invention. Correspondingly, the configuration of the different structures as well as there relative dimensions are intended to serve illustrative purposes only.

Figure 1:
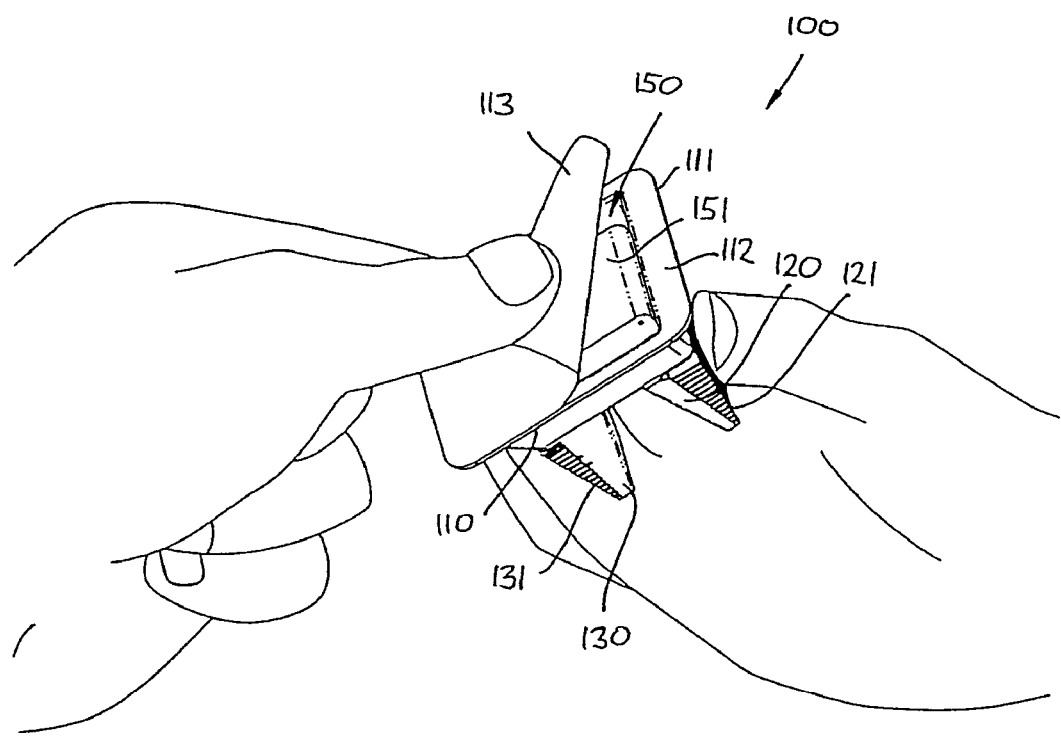
FIG. 1 shows in a perspective view a first embodiment of a medical device gripped by a user corresponding to a first state of use.

More specifically, FIG. 1 shows a first embodiment of a medical device 100 gripped by a user. The medical device comprises a second unit 110 with a housing defining an interior space, and a first unit 150 releasably attached within the interior space. In the following the second unit will also be termed the "inserter". The housing comprises a main portion with a lower opening surrounded by a circumferential flange 111 extending away from the housing, the flange having a lower surface 112 defining a general plane for the medical device. The housing further comprises first and second upwardly protruding actuation members (or handling members) 120, 130 arranged on the upper portion of the housing opposite the opening, the actuation members comprising ribbed portions 121, 131 allowing for easy gripping by a user, e.g. using the first and second fingers as shown. The first unit is in the form of a needle device (e.g. an infusion device or a sensor device) comprising an adhesive mounting surface 151 adapted for application to the skin of a subject, the mounting surface being generally planar and arranged substantially corresponding to the general plane. The needle device further comprises a needle (not shown) having a distal pointed end adapted to penetrate the skin of the subject, the needle having a first position in which the distal end is retracted relative to the mounting surface, and a second position in which the distal end projects relative to the mounting surface.

The inserter further comprises a foil member 113 which, when supplied to the user, is attached to the circumferential lower surface of the flange 111 thereby providing a sealed cavity in which the needle device is arranged. The foil member is further releasably attached to the adhesive means arranged on the mounting surface of the needle device. When the user intends to use the needle device, the foil member is peeled away as show in FIG. 1 whereafter the medical device 100 can be placed on a skin portion of the user (see FIG. 2A), the needle device thereby adhesively engaging the skin.

Figures 2A, 2B, 2C:
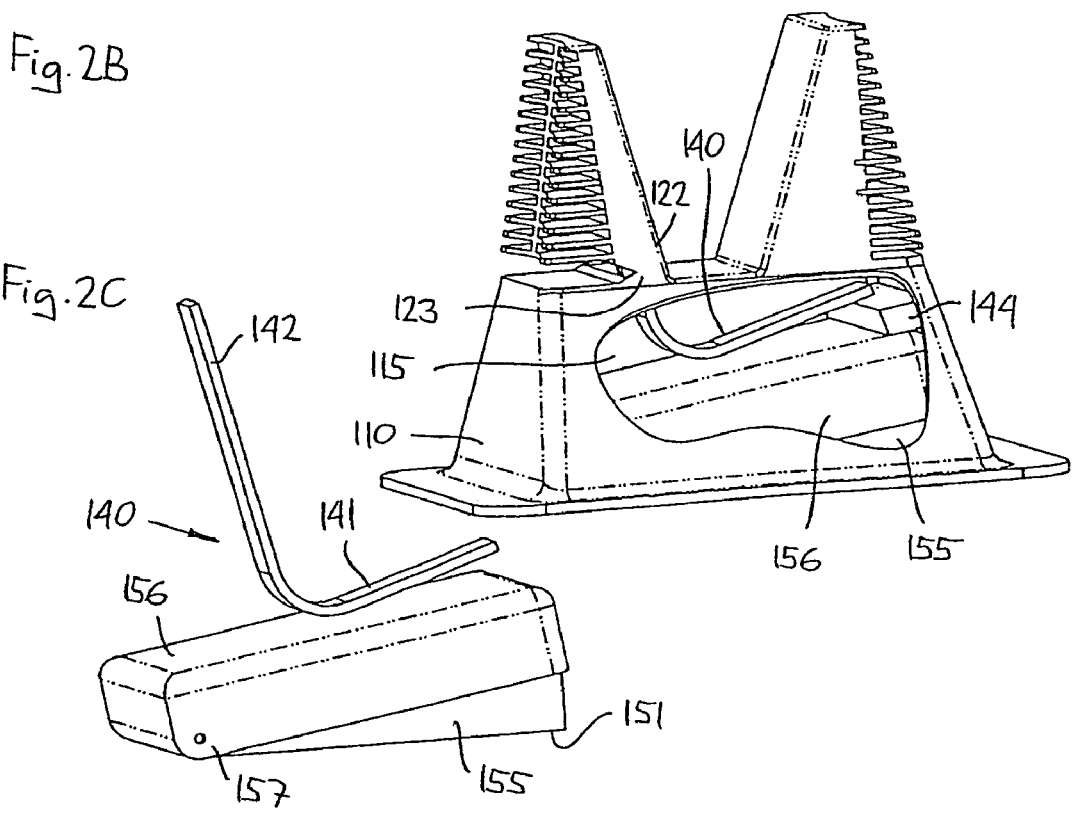
FIG. 2A shows in a perspective view the medical device of FIG. 1 gripped by the user corresponding to a second state of use.
FIG. 2B shows the needle device of FIG. 1A with an outer portion cut away.
FIG. 2C shows the first unit of the needle device of FIG. 1A.

Corresponding to the invention, the inserter further comprises actuatable driving means adapted to move the needle from the first position to the second position when the driving means is actuated with the second unit attached to the first unit. As best seen in FIG. 2B the driving means is in the form of an angularly bend leaf spring 140 comprising an upper portion 142 extending into the interior of the first actuation member 120 and a lower portion 141 with a distal end which in an initial state rests on a shelf member 144 protruding inwardly from the housing. In the initial state as supplied to the user, the spring is preferably in a relaxed condition and the spring may be held in place merely in cooperation with the first actuation member and the shelf, however, to prevent the spring from disengaging after actuation (see below) the upper portion may be attached to the first actuation member. The first actuation member is pivotably attached to the main portion by an integrally formed hinge 122. To prevent unintentional movement of the first actuation member and serving as tamper evidence, breakable locking means 123 is provided between the first actuation member and the main portion.

As best seen in FIG. 2C, the needle device comprises a lower base portion 155 defining the mounting surface, and an upper housing portion 156 pivotably attached to the base portion by hinge means 157. The needle is fixedly attached to the housing portion, the mounting surface comprising an opening (not shown) through which the needle can be advanced from its first to its second position when the housing portion is moved from an initial upper position to a lower engagement position. Between the two portions is arranged locking means (not shown) allowing the housing portion to be locked to the base plate when moved into engagement therewith.

After having placed the medical device on a skin portion, the user presses the actuation members towards each other to activate the driving means, thereby breaking the locking means as shown in FIG. 3A. In an alternative embodiment (not shown) the locking means may be collapsible. During this action the first actuation member is moved from a first (initial) position (or condition) through an intermediate position to a second position, during which movement of the first actuation member from the first to the intermediate position causes activation of the spring, and actuation of the first actuation member from the intermediate to the second position causes release of the activated spring thereby moving the needle from the first position to the second position. More specifically, corresponding to the intermediate condition, the leaf spring has been bent but the lower portion 141 is still resting on the shelf 144 (see FIG. 3B) whereby energy is elastically stored in the spring. Corresponding to the second condition the spring is released from the shelf, the lower portion of the spring thereby being forced downwardly engaging the upper surface of the housing portion 156, whereby the latter is pivoted downwardly into locking engagement with the base portion 155 as shown in FIGS. 4B and 4C. During this action the needle is moved from its first to its second position, the pointed distal end thereby being introduced through the skin of the user. As seen in FIG. 3B the inserter comprises a protrusion 145 which in the initial state is in engagement with a corresponding depression on the housing portion 156 thereby serving (in combination with similar opposed means (not shown) as a releasably attachment means between the two units.

Figure 4A:
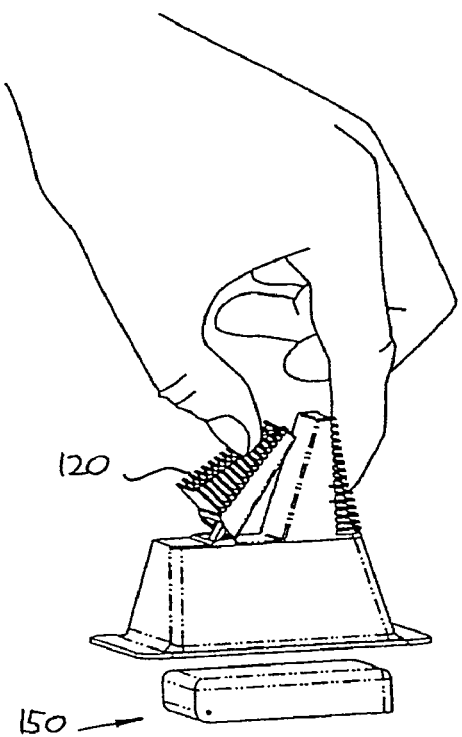
FIGS. 4A-4C shows a fourth state of use corresponding to FIGS. 2A-2C.
Figure 4B:
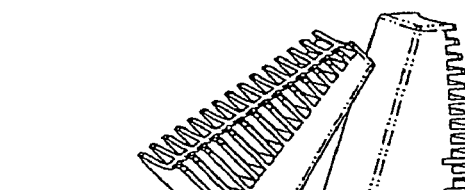
Figure 4C:
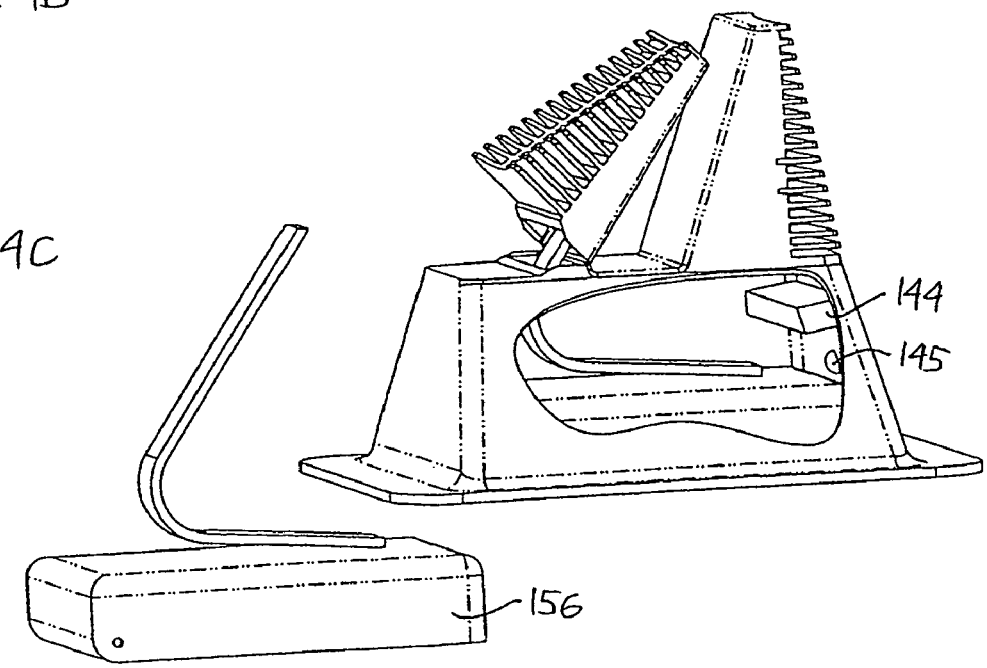
Figure 5:
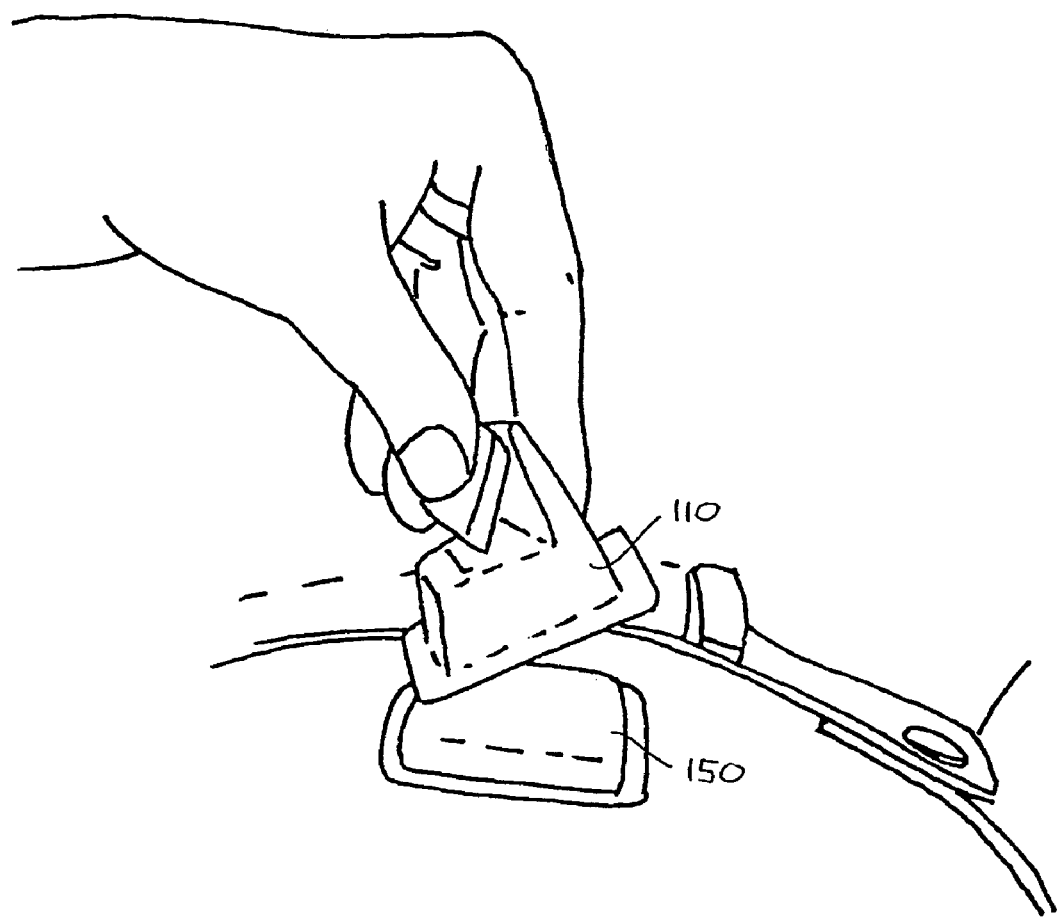
FIG. 5 shows in a perspective view the medical device of FIG. 1 gripped by the user corresponding to a fifth state of use.

When the needle has been introduced the inserter can be removed as shown in FIG. 4A. FIG. 5 shows the same situation seen from the perspective of the user when the needle device has been placed on the abdomen.

Figure 6A:
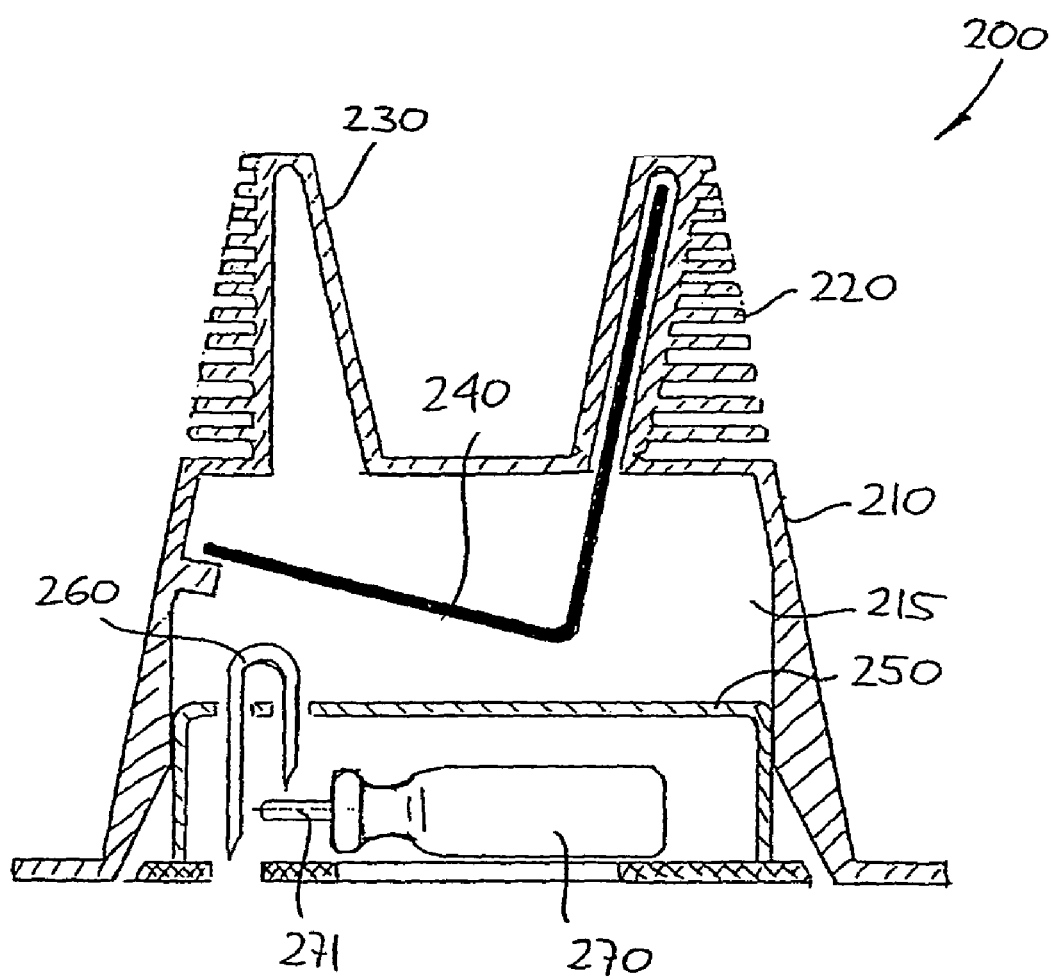
FIG. 6A shows in cross-section a second embodiment of a medical device.

In the first embodiment the needle was attached to an upper housing portion which was moveably arranged relative to the mounting surface, thereby providing the relative movement between the needle and the mounting surface. In FIG. 6A is shown a second embodiment of a medical device 200 substantially corresponding to the first embodiment, the device comprising an inserter 210 coupled to an infusion device comprising a hollow infusion needle 260, a drug-containing cartridge 270 as well as expelling means (not shown) arranged therewithin. However, in contrast to the first embodiment, merely the needle is moveable relative to the mounting surface. In the shown schematic embodiment the needle is bent in a U-form with the U-portion protruding through an upper surface of the infusion device, the needle further comprising a pointed distal end adapted to penetrate the skin of the user and a pointed proximal end adapted to penetrate a needle-penetratable sealing member 171 of the cartridge. In alternative embodiments the needle may be arranged within the infusion device, additional means being adapted to transfer the movement of the spring to the needle. In respect of use and actuation of the medical device, the second embodiment corresponds to the above-described first embodiment.

Figure 6B:
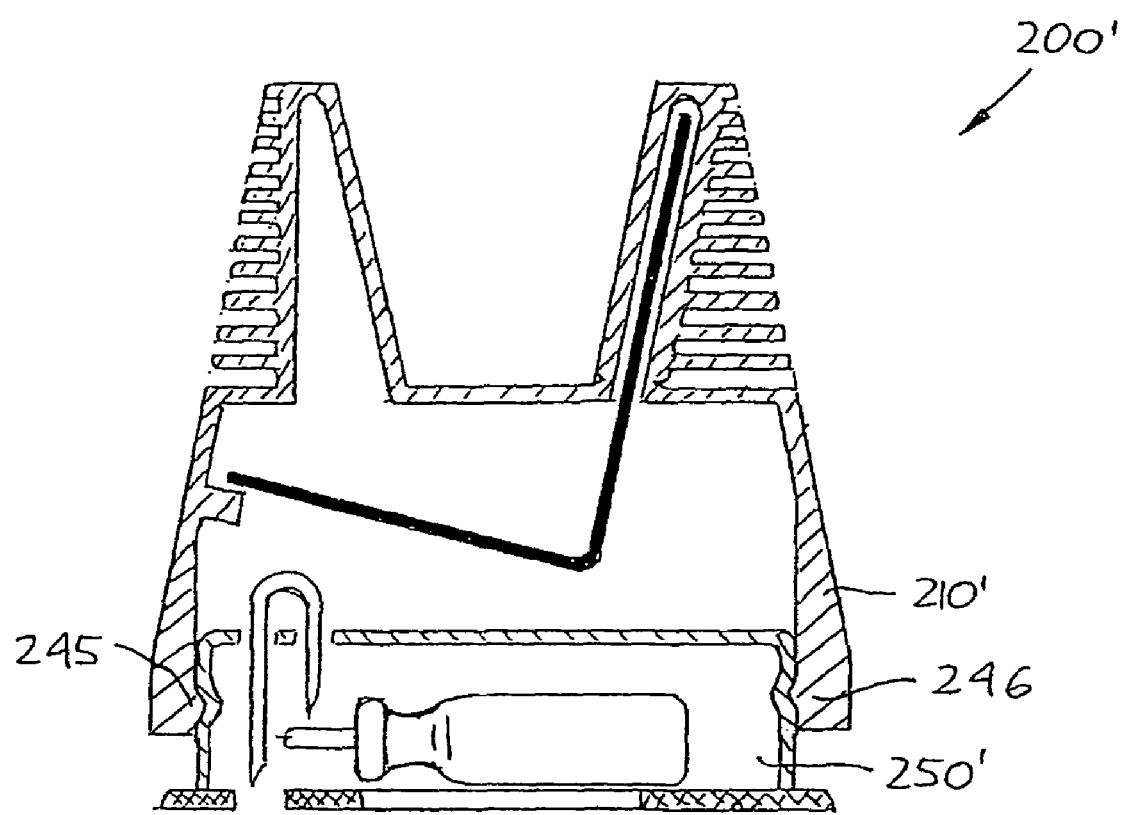
FIG. 6B shows an alternative configuration of the second embodiment.

In FIG. 6B is shown an alternative configuration 200' of the second embodiment in which the needle device 250' is only partially arranged within the housing 210', the surrounding flange and the foil sheet correspondingly being omitted. Further, the inserter comprises protrusions 245, 246 in engagement with corresponding depressions on the housing portion of the needle device thereby serving as a releasably attachment means between the two units. As appears, this configuration requires an additional packaging but is otherwise similar to the embodiment of FIG. 6A.

In the first and second embodiments the needle was moveably attached relative to the mounting surface, thereby providing the relative movement between the needle and the mounting surface and thereby the skin surface, however, the relative movement between the needle and the skin surface may also be provided by using the driving means to move a needle device comprising a protruding needle into contact with the skin surface, the needle device having a first (initial) position in which the mounting surface is retracted relative to the skin when the medical device is placed against the skin of a user, and a second position in which the mounting surface has been moved into engagement with the skin, the needle thereby penetrating the skin.

Figure 7:
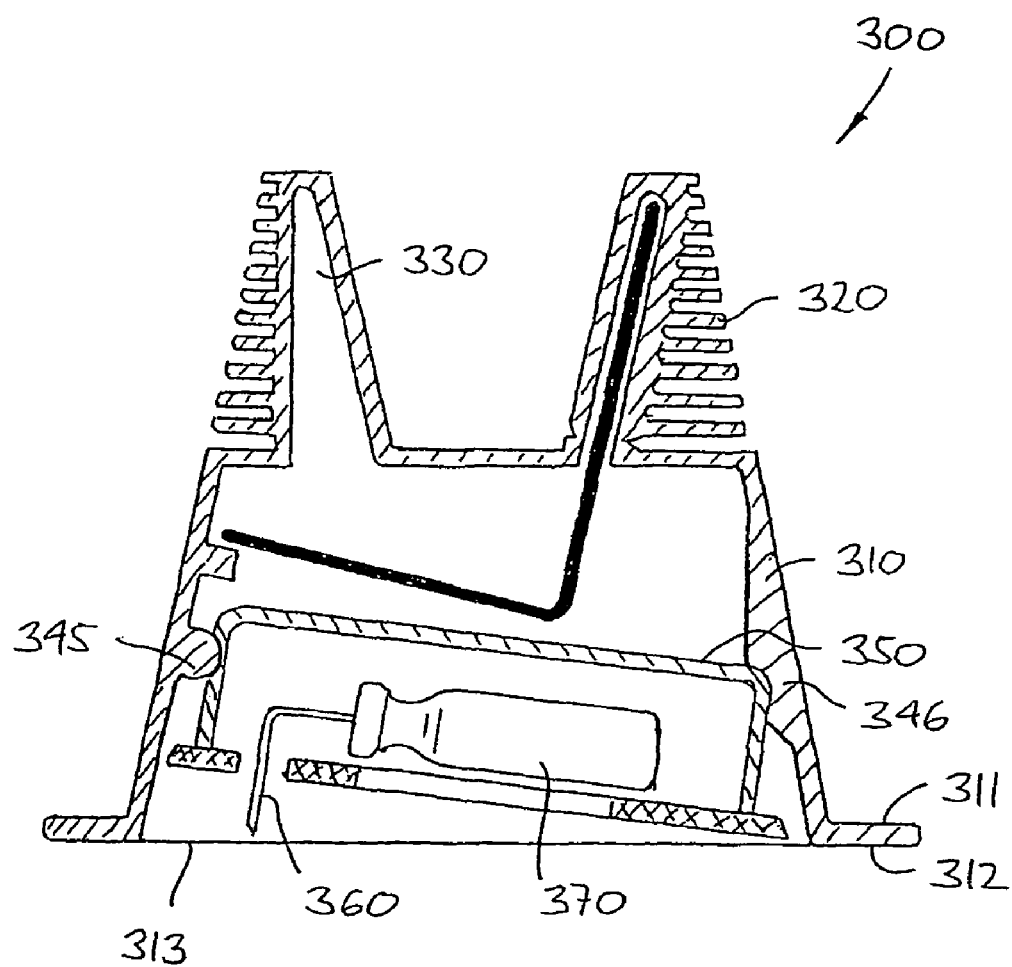
FIG. 7 shows in cross-section a third embodiment of a medical device.

Thus, in FIG. 7 is shown a third embodiment of a medical device 300 substantially corresponding to the first embodiment, the device comprising an inserter 310 coupled to an infusion device 350 comprising a hollow infusion needle 360 protruding from a mounting surface of the infusion device, a drug-containing cartridge 370 as well as expelling means (not shown) arranged therewithin. However, in contrast to the first embodiment, the mounting surface is initially arranged in a retracted position relative to the general plane defined by the lower surface 312 of the flange. As appears, the infusion device is arranged in an inclined position, this allowing the infusion device to be pivoted into its second skin-contacting position in a well controlled way. When comparing the first and third embodiment, it appears that the infusion device 350 corresponds to the upper housing portion 156, both members being arranged in an inclined position and comprising a fixedly attached needle. The inserter comprises gripping means 345, 346 in engagement with corresponding areas on the housing portion of the needle device thereby serving as a releasably attachment means between the two units.

The protruding portion of the needle is preferably supplied to the user with a protecting member (not shown). When the device is to be used, the user removes the sealing foil member 313, the peelable liner (not shown) covering the adhesive on the mounting surface as well as the needle protecting member, after which the medical device can be placed against the skin of the user corresponding to the situation shown in FIG. 2A. The liner may be coupled to the foil allowing the two members to be removed in one operation. In respect of actuation of the medical device, the third embodiment substantially corresponds to the above-described first embodiment, the main difference being that the base portion (and thereby the mounting surface) initially is attached to the housing portion forming a unitary infusion device.

Figure 8A:
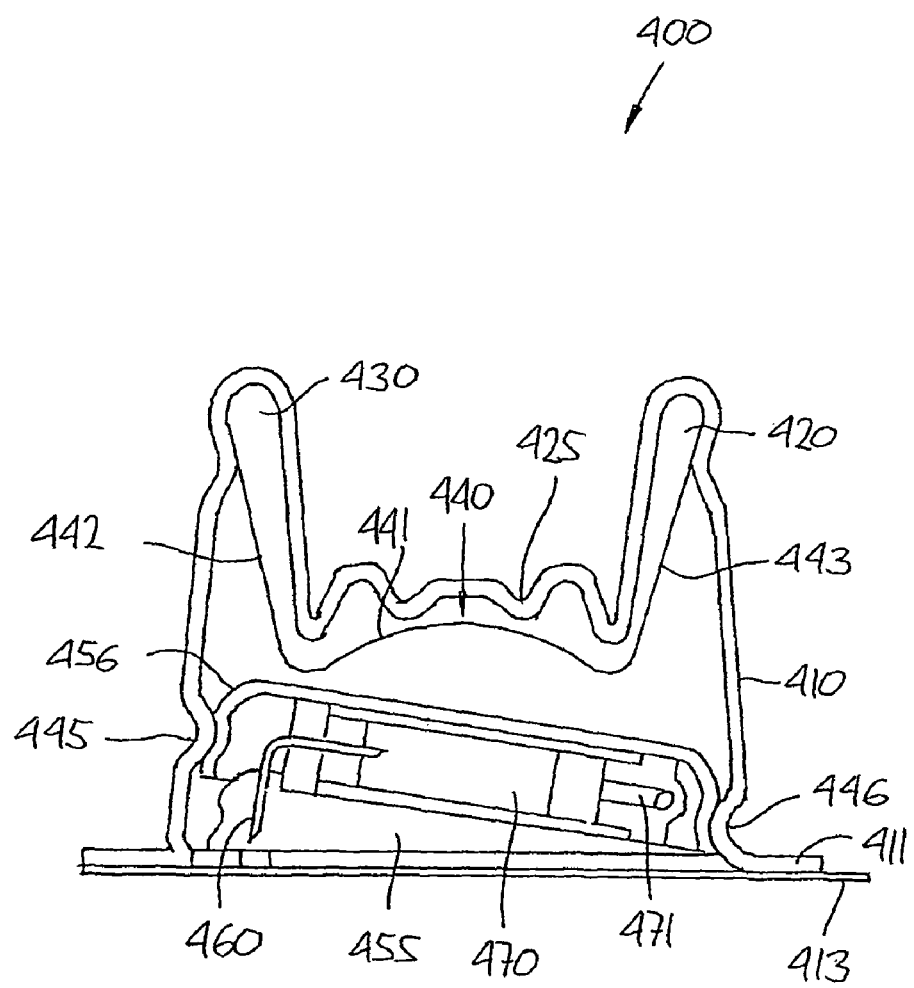
FIG. 8A shows in cross-section a fourth embodiment of a medical device.

In FIG. 8A is shown a fourth embodiment of a medical device 400 substantially corresponding to the first embodiment, the device comprising an inserter 410 coupled to an infusion device 450, the infusion device comprising a hollow infusion needle 460 mounted in an upper housing portion 456 and arranged in a retracted position relative to a base portion 455, and a drug-containing cartridge 470 proximally provided with a conduit 471 in communication with gas generating expelling means (not shown) arranged therewithin.

Whereas the inserter of the first embodiment is suitable for manufacture using injection molding, the inserter of the forth embodiment has been adapted for thermoforming, i.e. corresponding to the method often used for cost effective manufacture of packaging materials.

More specifically, the inserter comprises a lower opening surrounded by a circumferential flange 411 to which a seal member 413 is releasably attached, and two upwardly protruding substantially identical actuation members 420, 430 between which is provided a number or grooves 425 allowing the two actuation members to be pressed against each other. The inserter further comprises a first set of inwardly protruding members 445, 446 adapted to engage corresponding recesses on the infusion device, and a second set of inwardly protruding members 422, 432 adapted to hold a spring in place. The spring is in the form of a bi-staple leaf spring comprising an initially upwardly curved central portion 441 and two upwardly protruding leg portions 442, 443 arranged within the actuation members.

After having removed the seal member 413 and the liner protecting the adhesive, the medical device 400 is placed on a skin portion of the user. The user presses the two actuation members towards each other to activate the driving means. During this action the actuation members are moved from a first (initial) position (or condition) through an intermediate position to a second position, during which the spring is activated and released. More specifically, corresponding to the intermediate condition, the two leg portions have been moved towards each other thereby tensioning the curved portion of the spring, however, corresponding to the second condition the bi-stable spring suddenly transforms into its second bi-stable state whereby the curved portion is forced downwardly engaging the upper surface of the infusion device, whereby the latter is pivoted downwardly into engagement with the base portion whereby the needle is introduced through the skin of the user. As the second bi-stable state is only semi-stable, the spring will return to its initial position as the user reduces the compression force on the actuation members, however, this will not influence the infusion device. When the needle thus has been introduced the inserter can be removed.

Figure 8B:
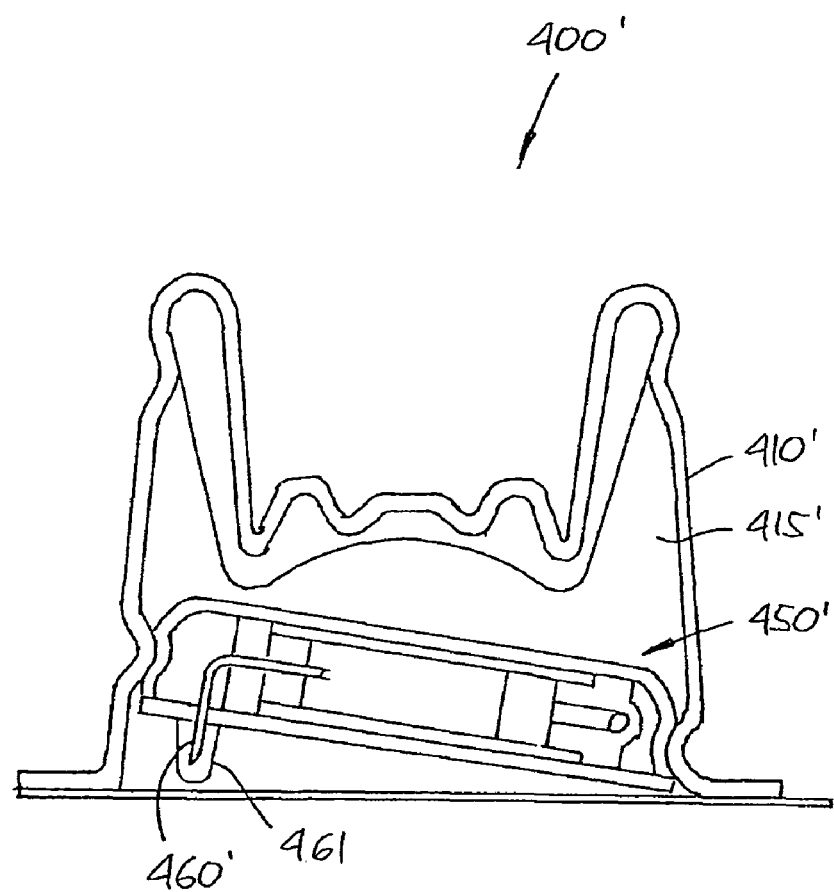
FIG. 8B shows a variant of the fourth embodiment.

In FIG. 8B is shown an alternative configuration of the fourth embodiment in which the needle device 450' is of the same overall configuration as the third embodiment, i.e. the needle device comprises a needle 460' initially protruding from the mounting surface (in this embodiment provided with a protecting cover 461 which has to be removed by the user prior to application of the device to the skin), the needle device being arranged inclined in a retracted position within the cavity 415' of the housing 410'. Otherwise the two alternatives are substantially identical in construction and use.

In the above described embodiments the needle (or the member comprising the needle) has been held in its non-actuated state by frictional means or gripping means, however, in an alternative configuration additional releasable locking means (not shown) may be provided. In advantageous embodiments such locking means is coupled to the user actuatable actuation means such that the locking means is released in combination with actuation of the driving means. Such locking means may be formed as a separate member or may be formed integrally with either a housing or a spring member.

Figure 9:
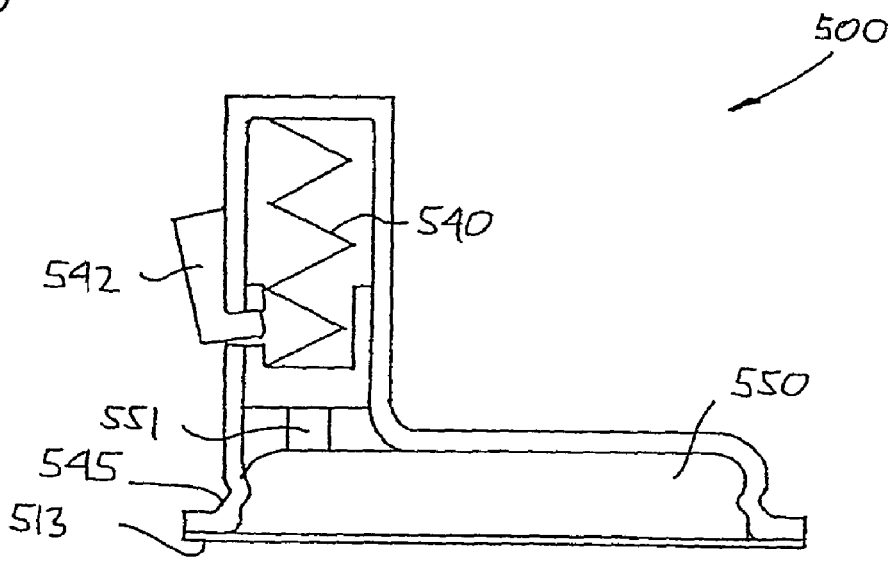
FIG. 9 shows in cross-section a fifth embodiment of a medical device.

FIG. 9 shows a fifth embodiment of a medical device 500 in which the driving means is (or can be) arrested in an activated state before being released by the user. The needle device 550 substantially corresponds to the second embodiment, i.e. merely the needle is moveable relative to the mounting surface, the needle being associated with additional transfer means 551 protruding from the upper surface of the needle device and adapted to be engaged by the drive means.

The inserter comprises a drive means in the form of a spring actuated piston assembly 540, 541 acting on the transfer means, however, any suitable type of drive means may be utilized, e.g. any elastically compressible or deformable driving means, e.g. metal or polymer members, elastomeric foam or gas. In the shown embodiment the medical device is supplied to the user as a sealed unit with the spring in a pre-tensioned state, the inserter being provided with user actuatable release means 542 allowing the user to release the spring after the device has been placed on a skin portion of the user as discussed above. Advantageously, the release means may be designed to allow the combined device to be provided in a sterilized and sealed condition (not shown).

In an alternative embodiment (not show) the inserter may be supplied with the spring in a non-tensioned state, the inserter comprising means allowing the user to activate and lock the spring in an activated state. In a further alternative embodiment (not show) such an inserter may be supplied as a separate unit in which the needle device is mounted by the user. In this way the inserter can be provided as a durable unit.

Figure 10:
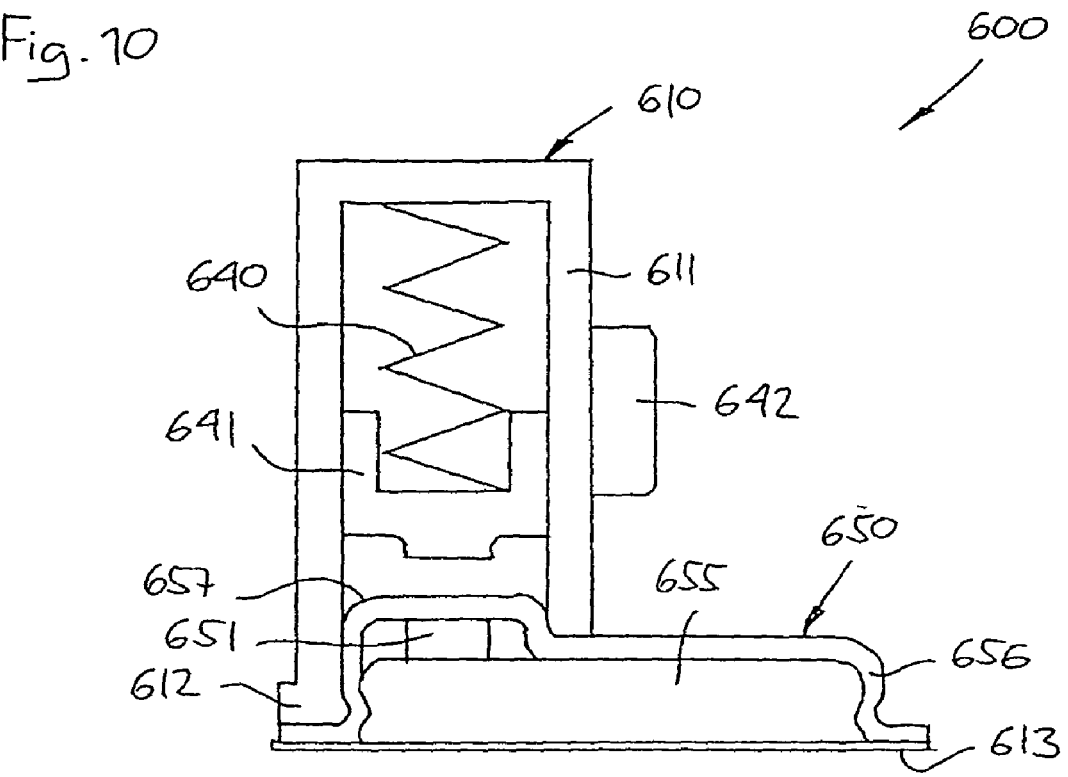
FIG. 10 shows in cross-section a sixth embodiment of a medical device.

FIG. 10 shows a sixth embodiment of a medical device 600 substantially corresponds to the fifth embodiment, however, the inserter is provided as a separate unit adapted to engage a needle device provided as a sealed unit.

More specifically, the needle device 650 resembles the combined device of the fifth embodiment (i.e. comprising a needle device and a casing therefore), however, the driving means has been omitted allowing the needle device to be supplied as a compact, sterilized and sealed unit comprising a needle device 655 and an outer housing (e.g. in the form of the closed packaging) 656, 613, the unit being adapted to be mounted in a separate inserter 610. The inserter comprises a housing 611 adapted to engage the outer housing of the needle device and comprises a drive means 640, 641, 642 corresponding to the fifth embodiment, i.e. a lockable, spring-driven piston adapted to engage the transfer means 651 through a deformable portion 657 of the outer housing. The two units may be provided with releasable gripping means 612 allowing the inserter to be attached to the needle device prior to arranging the needle device on a skin portion, this improving handling. Correspondingly, the user may place the needle device 650 in the inserter before removing the protective foil 613. The inserter may be supplied separately as a durable unit or it may be supplied as part of a kit, e.g. a package containing a plurality of needle devices and an inserter. Indeed, the transfer means may also be actuated manually by the user by simply applying pressure with a finger.

In an alternative embodiment (not shown) the needle device is arranged in an inclined position corresponding to FIGS. 8A and 8B, albeit without driving means arranged within the outer housing. For such an arrangement the inserter 610 would engage a deformable portion of the outer housing whereby the needle device would be pivoted against the skin of the user. In a further alternative embodiment (not shown) the gripping means holding the needle device in its inclined position (corresponding to the inwardly protruding member 445 in FIG. 8A) may be formed as a detent which would hold back the needle device until a certain threshold level for the detent is exceeded when the user applies an insertion force to the flexible outer housing, this arrangement providing a simple means to allow swift and comfortable insertion.

In the above-described embodiments a medical device has been described comprising a reservoir, however, for better illustrating the principles of the present invention, the means for expelling a drug from the reservoir has been omitted in the figures. Such expelling means, which as the reservoir does not form part of the present invention in its basic form, may be of any type which would be suitable for arrangement within a skin-mountable drug delivery device. Further, as the needle of the present invention also may be in the form of a needle sensor, the interior of the medical device may comprise sensor means adapted to cooperate with the needle sensor.

Figure 11A:
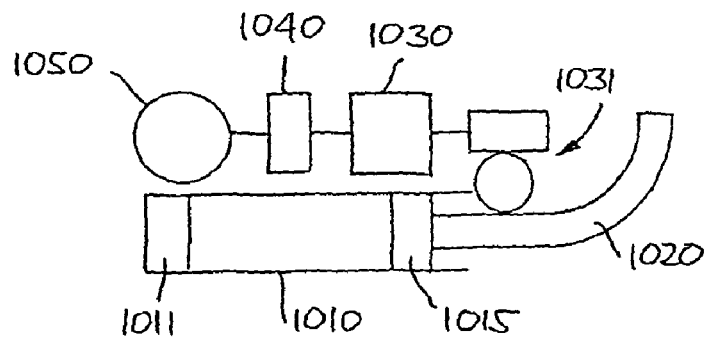
FIGS. 11A-11D shows different expelling means suitable for use with the invention.

In FIGS. 11A-11D examples of expelling means suitable for use with the present invention are shown schematically, however, these are merely examples. More specifically, FIG. 11A shows a pump arrangement comprising a drug-containing cartridge 1010 having a distal closure member 1011 allowing a needle to be connected, and a piston 1015 slidingly arranged there within, a flexible toothed piston rod 1020 (for example as disclosed in U.S. Pat. No. 6,302,869), an electric motor 1030 which via a worm-gear arrangement 1031 drives the piston rod to expel drug from the cartridge, the motor being controlled by control means 1040 and the energy for the control means and the motor being provided by a battery 1050. The pump may be activated when the needle is inserted (by means not shown) or by separate user-actuatable means (not shown) after the inserter has been detached form the delivery device.

Figure 11B:
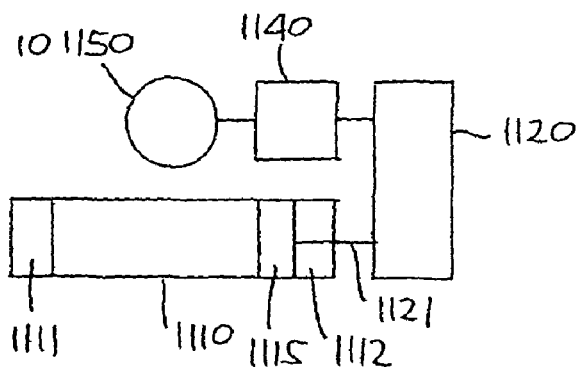

FIG. 11B shows a pump arrangement comprising a drug-containing cartridge 1110 having distal and proximal closure members 1111, 1112, and a piston 1115 slidingly arranged there within, gas generating means 1120 in fluid communication with the interior of the cartridge via conduit 1121 for driving the piston to expel drug from the cartridge, the gas generating means being controlled by control means 1140 and the energy for the control means and the gas generation being provided by a battery 1150. The pump may be activated as indicated above. A detailed disclosure of such gas generating means for a drug delivery device can be found in e.g. U.S. Pat. No. 5,858,001.

Figure 11C:
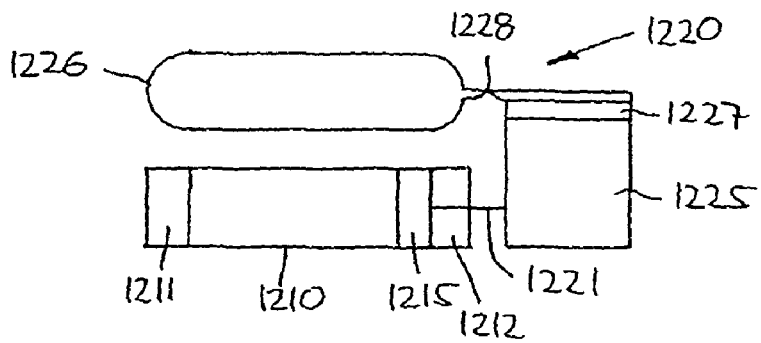

FIG. 11C shows a pump arrangement comprising a drug-containing cartridge 1210 having distal and proximal closure members 1211, 1212, and a piston slidingly 1215 arranged there within, an osmotic engine 1220 in fluid communication with the interior of the cartridge via conduit 1221 for driving the piston to expel drug from the cartridge. The osmotic engine comprises a first rigid reservoir 1225 containing a salt-solution and a second collapsible reservoir 1226 containing water, the two reservoirs being separated by a semipermeable membrane 1227. When supplied to the user, the fluid connection 1228 between the second reservoir and the membrane is closed by a user-severable membrane (e.g. a weak weld) which, when severed, will allow the osmotic process to start as water is drawn from the second reservoir through the membrane and into the first reservoir. The pump may be activated as indicated above. A detailed disclosure of the osmotic drive principle can be found in e.g. U.S. Pat. No. 5,169,390.

Figure 11D:
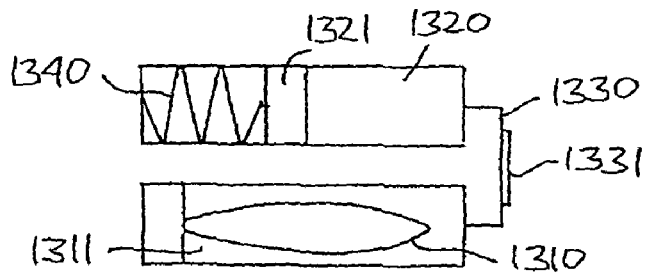

FIG. 11D shows a pump arrangement comprising a drug-containing flexible reservoir 1310 arranged within a rigid fluid-filled secondary reservoir 1311 in fluid communication with a primary reservoir 1320 through a conduit 1330 comprising a flow restrictor 1331. The primary reservoir is in the form of a cartridge with a moveable piston 1321 and contains a viscous drive fluid. A spring is arranged to act on the piston to drive fluid from the first to the second reservoir thereby expelling drug from the flexible reservoir when the latter is connected to an infusion needle (not shown). The flow rate will be determined by the pressure generated by the spring in the drive fluid, the viscosity of the drive fluid and the flow resistance in the flow restrictor (i.e. bleeding hole principle). The pump may be activated by straining the spring or by releasing a pre-stressed spring, either when the needle is inserted (by means not shown) or by separate user-actuatable means (not shown) after the inserter has been detached form the delivery device. An example of this principle used for drug infusion is known from DE 25 52 446. In an alternative configuration, the drug reservoir may be pressurized directly to expel the drug via a flow restrictor, e.g. as disclosed in U.S. Pat. No. 6,074,369.

In the above described embodiments, the needle has been in the form of a unitary needle device (e.g. an infusion needle or a needle sensor), however, a needle device may also be introduced subcutaneously in combination with an insertion needle which is withdrawn after insertion thereof.

Figure 12A:
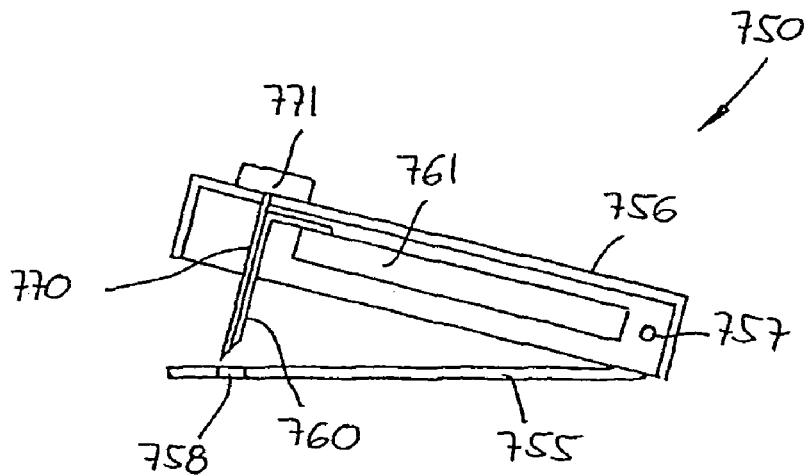
FIGS. 12A-12C shows different states of use for a sensor device.
Figure 12B:
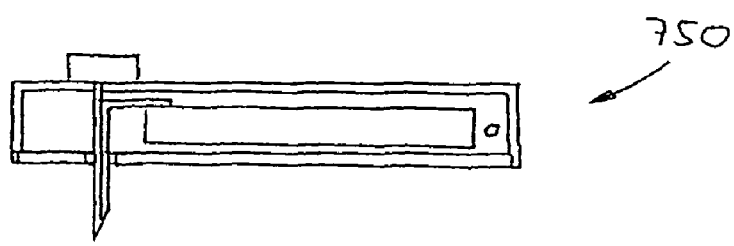
Figure 12C:
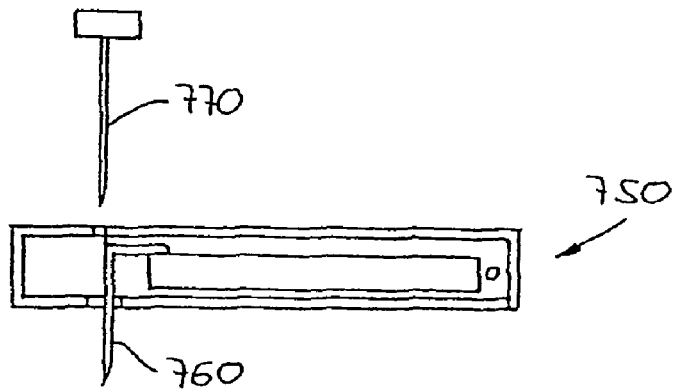

With reference to FIGS. 12A-12C an embodiment of a sensor device will be described, having the same general hinged configuration as the needle device of the first embodiment, wherein the needle is in the form of a combined needle sensor and corresponding insertion needle therefore. For improved clarity, the structures relating to the inserter have been omitted in the drawings.

More specifically, the sensor device 750 comprises a lower base portion 755 defining the mounting surface, and an upper housing portion 756 pivotably attached to the base portion by hinge means 757. A relatively flexible needle-formed sensor 760 with a distal sensor element is fixedly attached to the housing portion and is in communication with signal receiving means 761. The signal receiving means may be contact means for connecting the sensor device to external processor means for evaluating the signals, transmitting means for wireless transmission to an external processor, or a processor arranged within the housing. The needle-sensor is supported by an insertion needle 770, the support preventing deformation of the needle-sensor during insertion. The insertion needle is slidably received in the upper housing portion and comprises a gripping member 771 allowing the insertion needle to be withdrawn by the user after insertion has taken place. The mounting surface comprises an opening 758 through which the two needles can be advanced from its first to its second position when the housing portion is moved from an initial upper position to a lower engagement position. Between the two portions is arranged locking means (not shown) allowing the housing portion to be locked to the base plate when moved into engagement therewith.

FIG. 12A shows the sensor device in an initial position, FIG. 12B shows the sensor device after the two needles 760, 770 have been introduced and the inserter has been removed, and FIG. 12C shows the situation in which the needle-sensor has been inserted and the insertion needle has been withdrawn. In the shown embodiment the insertion needle is adapted to be withdrawn by the user, however, the driving means and the gripping means may be designed to engage each other such that the insertion needle is removed from the sensor device together with the inserter as shown in FIG. 13C.

In FIG. 13A is shown a schematic representation of a further embodiment of a medical device 800 substantially corresponding to the embodiment shown in FIG. 6, the device comprising an inserter 810 coupled to an infusion device 850 comprising a flexible infusion cannula 860 adapted to cooperate with a pointed insertion needle 880 mounted on the leaf spring 840 by means of a needle carrier 881, a drug-containing cartridge 870 as well as expelling means (not shown) arranged there within. The flexible cannula (which e.g. may be of the soft "Teflon®" type) comprises a self-sealing needle-penetratable septum portion 861 through which the insertion needle is mounted as well a circumferentially arranged locking means in form of a collar 862. In the initial position the pointed distal end of the insertion needle is arranged in a slightly retracted position relative to the distal opening of the infusion cannula and with the needle carrier positioned a small distance above the septum. When the inserter is actuated as shown in FIGS. 2-4, the needle carrier is moved downwardly thereby engaging the septum, in which position the insertion needle projects a small distance out through the cannula, and further forcing the cannula from its retracted to its extended position, the projecting pointed needle end allowing the cannula to be introduced through the skin of a subject, see FIG. 13B. In this position the locking means engages the housing of the medical device allowing the insertion needle to be removed from the device together with the inserter as seen in FIG. 13C.

In an alternative embodiment (not shown) the needle device is in the form of a so-called infusion set comprising an infusion cannula and a therethrough arranged removable insertion needle, such infusion sets typically being used to provide an infusion site in combination with (durable) infusion pumps.

When the above-described needle devices are in the form of an infusion pumps or sensor devices, the pump (i.e. delivery means) or sensor electronics will have to be actuated in combination with insertion of the needle. This actuation may take place in combination with the above-described actuation of the needle (e.g. by closing an electric contact or by providing a fluid communication) or it may take place using additional actuation means which may be operated separately after the device has been mounted on the skin and the needle introduced.

In the shown embodiments the medical device has been a unitary structure which may be provided fully enclosed within the second member, however, the second unit may be adapted to receive a further unit engaging the first unit. For example, the second unit may comprise an opening (e.g. closed by a breakable seal) through which the further unit can be inserted into second unit to thereby engage the first unit. In this condition the medical device can then be used as described above. In such an arrangement, the first unit may be in the form of a skin-mountable patch comprising a transcutaneous device, and the further unit may be a drug delivery device connectable to the patch.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

CITED DOCUMENTS

U.S. Pat. No. 4,340,048
U.S. Pat. No. 4,552,561
U.S. Pat. No. 5,858,001
U.S. Pat. No. 6,280,148
U.S. Pat. No. 5,957,895
U.S. Pat. No. 5,527,288
U.S. Pat. No. 2,605,765
U.S. Pat. No. 4,340,048
EP 1 177 802
U.S. Pat. No. 5,814,020
U.S. Pat. No. 5,931,814
WO 02/15965
U.S. Pat. No. 5,482,473
U.S. Pat. No. 5,390,671
U.S. Pat. No. 5,391,950
U.S. Pat. No. 5,568,806
U.S. Pat. No. 5,954,643

The invention claimed is:

1. A medical device comprising a first unit and a releasably attached or attachable second unit, the first unit comprising:
   a mounting surface adapted for application to the skin of a subject,
   a transcutaneous device comprising a distal pointed end adapted to penetrate the skin of the subject,
   the transcutaneous device having a first position in which the distal end is retracted relative to the mounting surface, and a second position in which the distal end projects relative to the mounting surface, the second unit comprising:
   actuatable driving means comprising a spring means adapted to move the transcutaneous device from the first position to the second position when the driving means is actuated with the second unit attached to the first unit,
   actuation means actuatable from a first condition through an intermediate condition to a second condition,
   wherein the spring means is provided in an unbiased condition and whereby actuation of the actuation means from the first to the intermediate condition causes activation of the spring means, and actuation of the actuation means from the intermediate to the second condition causes release of the activated spring means thereby moving the transcutaneous device from the first position to the second position.

2. A medical device as defined in claim 1, wherein the actuation means comprises an actuating element which is moved from a first position through an intermediate position to a second position, preferably corresponding to a substantially non-composite movement.

3. A medical device as defined in claim 1, wherein actuation of the actuation means from the first through the intermediate to the second condition is accomplished by moving two actuation elements relative to each other, preferably against each other.

4. A medical device as defined in claim 3, wherein the transcutaneous device is associated with transfer means upon which the driving means acts to thereby move the transcutaneous device.

5. A medical device as defined in claim 2, wherein the driving means can be locked in its activated state.

6. A medical device as defined in claim 1, wherein the driving means comprises spring means which is or can be arranged in an activated state, the second unit comprising trigger means for releasably retaining the spring means in the actuated state, the trigger means being operable to release the spring means for moving the transcutaneous device from the first position to the second position.

7. A medical device as defined in claim 1, wherein the second unit has an interior space for at least partially accommodating the first unit and an opening through which the first member can be moved when detached from the second unit, the mounting surface facing away from the interior space.

8. A medical device as defined in claim 7, further comprising a seal member, the opening being surrounded by a circumferential portion of the second unit to which portion the seal member is releasably attached, thereby providing a closed space for the first unit.

9. A medical device as defined in claim 8, wherein the second unit comprises a housing defining the interior space, the first unit comprising an upper portion facing towards the interior space, the driving means being arranged within the interior space between the upper portion and the housing.

10. A medical device as defined in claim 8, wherein the circumferential portion defines a general plane, the mounting surface being generally planar and arranged substantially corresponding to the general plane.

11. A medical device as defined in claim 1, wherein the mounting surface comprises adhesive means for attaching the first unit to the skin of the subject.

12. A medical device as defined in claim 8, wherein the mounting surface comprises adhesive means for adhering the first unit to the skin of the subject, the seal member being releasably attached to the adhesive means.

13. A medical device as defined in claim 1, wherein the transcutaneous device is a hollow infusion needle, the first unit further comprising:
   a reservoir adapted to contain a liquid drug and comprising in a situation of use an outlet in fluid communication with the infusion needle, and
   expelling means for expelling a drug out of the reservoir and through the skin of the subject via the hollow needle.

14. A medical device as defined in claim 1, wherein the transcutaneous device is in the form of a needle sensor comprising sensor means capable of being influenced by a body substance and producing a signal corresponding thereto.

15. A medical device as defined in claim 1, wherein the transcutaneous device is a cannula in combination with a pointed insertion needle accommodated at least partially within the cannula, the cannula having a distal opening,
   the cannula and insertion needle being arranged to be simultaneously moved by the driving means from their respective first position to their respective second position when the driving means is actuated,
   wherein the insertion needle is arranged to be moveable away from the distal opening when the cannula and the insertion needle have been moved to their second position.

16. A medical device as defined in claim 15, wherein the cannula comprises a needle-penetratable septum through which the insertion needle is arranged when the cannula and the insertion needle is moved from their respective first position to their respective second position.

17. A medical device as defined in claim 1, wherein the transcutaneous device is a longitudinal sensor device in combination with a pointed insertion needle arranged to support a distal portion of the sensor device,
   the sensor device and insertion needle being arranged to be simultaneously moved by the driving means from their respective first position to their respective second position when the driving means is actuated,
   wherein the insertion needle is arranged to be moveable away from the distal portion when the sensor device and the insertion needle have been moved to their second position.

18. A medical device as defined in claim 15, wherein the insertion needle in its second position is attached to the second unit, whereby removal of the second unit from the first unit withdraws the insertion needle therefrom.

19. A medical device as defined in claim 1, wherein the driving means in its activated state is not stable.

* * * * *